(12) United States Patent
Kim et al.

(10) Patent No.: US 8,389,492 B2
(45) Date of Patent: Mar. 5, 2013

(54) LYOPHILIZED DNA FORMULATIONS FOR ENHANCED EXPRESSION OF PLASMID DNA

(75) Inventors: Jong-Mook Kim, Seoul (KR); Sujeong Kim, Seoul (KR); Woong Hahn, Goyang-si (KR); WonSun Yoo, Seoul (KR)

(73) Assignee: ViroMed Co., Ltd. (KR)

( * ) Notice: Subject to any disclaimer, the term of this patent is extended or adjusted under 35 U.S.C. 154(b) by 0 days.

(21) Appl. No.: 13/045,460

(22) Filed: Mar. 10, 2011

(65) Prior Publication Data

US 2011/0166211 A1 Jul. 7, 2011

Related U.S. Application Data

(62) Division of application No. 12/421,425, filed on Apr. 9, 2009, now abandoned.

(60) Provisional application No. 61/043,605, filed on Apr. 9, 2008.

(51) Int. Cl.
*A61K 31/7088* (2006.01)

(52) U.S. Cl. .................................................... 514/44 R

(58) Field of Classification Search .................. None
See application file for complete search history.

(56) References Cited

U.S. PATENT DOCUMENTS

| | | | |
|---|---|---|---|
| 5,328,836 A | 7/1994 | Shima et al. | |
| 5,500,354 A | 3/1996 | Kitamura et al. | |
| 5,587,359 A | 12/1996 | Higashio et al. | |
| 6,121,246 A | 9/2000 | Isner | |
| 6,248,722 B1 | 6/2001 | Morishita et al. | |
| 6,258,787 B1 | 7/2001 | Isner | |
| 6,316,419 B1 | 11/2001 | Leiden et al. | |
| 7,276,359 B1 | 10/2007 | Musunuri et al. | |
| 7,285,540 B2 | 10/2007 | Morishita et al. | |
| 7,323,297 B1 | 1/2008 | Szoka et al. | |
| 7,745,174 B2 | 6/2010 | Kim et al. | |
| 7,812,146 B2 * | 10/2010 | Kim et al. | 536/23.51 |
| 2003/0148968 A1 | 8/2003 | Hammond et al. | |
| 2003/0171287 A1 | 9/2003 | Morishita et al. | |
| 2003/0176347 A1 | 9/2003 | Nakamura et al. | |
| 2004/0105882 A1 | 6/2004 | Morishita et al. | |
| 2004/0228834 A1 | 11/2004 | Isner et al. | |
| 2005/0079581 A1 | 4/2005 | Kim et al. | |
| 2005/0164208 A1 | 7/2005 | Poulin | |
| 2006/0286072 A1 | 12/2006 | Giordano et al. | |
| 2008/0081366 A1 | 4/2008 | Musunuri et al. | |
| 2008/0268030 A1 | 10/2008 | Morishita et al. | |
| 2009/0004260 A1 | 1/2009 | Morishita et al. | |
| 2009/0082293 A1 | 3/2009 | Giordano et al. | |
| 2009/0130761 A1 | 5/2009 | Koyama et al. | |
| 2009/0131350 A1 | 5/2009 | Kim et al. | |
| 2009/0202606 A1 | 8/2009 | Kim et al. | |
| 2009/0258932 A1 | 10/2009 | Kim et al. | |
| 2012/0010273 A1 | 1/2012 | Kim et al. | |

FOREIGN PATENT DOCUMENTS

| | | | |
|---|---|---|---|
| CN | 1358543 A | | 7/2002 |
| EP | 0 838 221 A1 | | 4/1998 |
| EP | 1061955 B1 | | 5/2005 |
| EP | 1555033 A2 | | 7/2005 |
| JP | 2006-515855 | | 6/2006 |
| WO | WO 98/50079 A2 | | 11/1998 |
| WO | WO 99/45775 A1 | | 9/1999 |
| WO | WO 01/34208 A1 | | 5/2001 |
| WO | WO 02/089856 A1 | | 11/2002 |
| WO | WO03/078568 | * | 9/2003 |
| WO | WO 03/078568 A2 | | 9/2003 |
| WO | WO 2004/060059 A2 | | 7/2004 |
| WO | WO 2007/132873 A1 | | 11/2007 |

OTHER PUBLICATIONS

Yang et al. (Hepatology. Apr. 2001; 848-859).*
Brus et al (Journal of Controlled Release. 2004; 95: 119-131).*
Taniyama et al. (Gene Therapy. 2001; 8: 181-189).*
Jo, J. et al., "Liver Targeting of Plasmid DNA with a Cationized Pullulan for Tumor Suppression" *Journal of Nanoscience and Nanotechnology* 6(9/10): 2853-2859, American Scientific Publishers, United States (2006).
Morishita, R. et al., "Therapeutic Angiogenesis using Hepatocyte Growth Factor (HGF)" *Current Gene Therapy* 4:199-206, Bentham Science Publishers Ltd. (2004).
Nakagami, H. et al., "Hepatocyte growth factor as potential cardiovascular therapy" *Expert Rev. Cardiovasc. Ther.* 3(3):513-519, Future Drugs Ltd. (2005).
Sharma, V. and Klibanov, A., "Moisture-Induced Aggregation of Lyophilized DNA and its Prevention" *Pharmaceutical Research* 24(1): 168-175, Springer Science + Business Media, Inc., United States (2007).
English Abstract of CN Publication No. 1358543A, Publication Date: Jul. 17, 2002 cited as FP9.
Allison, S.D., and Anchordoquy, T.J., "Mechanisms of protection of cationic lipid DNA complexes during lyophilization" *Journal of Pharmaceutical Sciences* 89(5):682-691, Wiley-Liss and The American Pharmaceutical Association, United States (2000).
Anchordoquy, T., et al., "Low molecular weight dextrans stabilize nonviral vectors during lypholization at low osmolalities: Concentrating suspensions by rehydration to reduced volumes," *Journal of pharmaceutical sciences*, 94(6):1226-1236, American Pharmaceutical Association, (2005).
Brus C. et al., "Stabilization of oligonucleotide—polyethylenimine complexes by freeze-drying: physicochemical and biological characterization" *Journal of Controlled Release* 95:119-131, Elsevier B.V. (2004).

(Continued)

*Primary Examiner* — Scott Long

(74) *Attorney, Agent, or Firm* — Sterne, Kessler, Goldstein & Fox P.L.L.C.

(57) ABSTRACT

The present invention provides for a method of treating or preventing ischemic or liver disease in a subject by administering a composition reconstituted from a lyophilized hepatocyte growth factor (HGF) DNA formulation, where the DNA formulation comprises an HGF plasmid DNA, salt and a carbohydrate. The invention further provides for a method of making such a lyophilized DNA formulation that preserves or enhances gene expression both in vitro and in vivo, thus maintaining or stimulating the biological activity of the expressed protein. The invention also provides for the DNA formulation, or the lyophilized DNA formulation according to the methods disclosed.

20 Claims, 5 Drawing Sheets

OTHER PUBLICATIONS

Courtney, L., et al., "Homo sapiens PAC clone RP5-1098B1 from 7q11.223-q21, complete sequence," GenBank Database, Accession No. AC004960, 51 pgs. (1998).

Deng, et al., "Secretory Expression of the Deleted Variant of Human Hepatocyte Growth Factor (hdHGF) in *Pichia pastoris*," Chinese Journal of Biochemistry and Molecular Biology, 2001, 17:590-594, China Academic Journal Electronic Publishing House, Beijing, China. English Abstract is on face page of document.

Dimitriadis, G., "Entrapment of Plasmid DNA in Liposomes" *Nucleic Acids Research* 6(8):2697-2705, Information Retrieval Ltd., England (1979).

Kato, N., et al., "Nonviral HVJ (hemagglutinating virus of Japan) liposome mediated retrograde gene transfer of human hepatocyte growth factor into rat nervous system promotes functional and histological recovery of the crushed nerve," *Neuroscience Research* 52:299-310, Elsevier Ireland (2005).

Liu, Y., "The Human Hepatocyte Growth Factor Receptor Gene: Complete Structural Organization and Promoter Characterization," *Gene* 215:159-169, Elsevier, Netherlands (1998).

Liu. Y., et al., "Secretory Expression of the Deleted Variant of Human Hepatocyte Growth Factor in *Pichia pastoris*," *World Journal of Gastroenterology* 11(45):7097-103, World Journal of Gastroenterology, China (2005).

Miyazawa, K.., et al., "Molecular Cloning and Sequence Analysis of cDNA for Human Hepatocyte Growth Factor," *Biochem.Biophys. Res. Commun.* 163:967-973, Academic Press (1989).

Nakamura, T., et al., "Molecular cloning and expression of human hepatocyte growth factor," *Nature* 342:440-443, Macmillan Journals Ltd. (1989).

Pdxon, Scott W. and Hughes, Jeffery A., "The effect of lypholization on plasmid DNA activity," *Pharmaceutical development and technology* 5(1)115-122, Informa Healthcare, United States (2000).

Rubin, J., et al., "A broad-spectrum human lung fibroblast-derived mitogen is a variant of hepatocyte growth factor," *Proc. Natl. Acad. Sci. USA* 88:415-419, Proceedings of the National Academy of Sciences of the United States of America, United States (1991).

Seki, T., et al., "Isolation and Expression of cDNA for Different Forms of Hepatocyte Growth Factor from Human Leukocyte," *Biochem. Biophys. Res. Commun.* 172:321-327, Academic Press (1990).

Seki, T., et al., "Organization of the human hepatocyte growth factor-encoding gene," *Gene* 102(2):213-219, Elsevier, Netherlands (1991).

Shima, N., et al., "Hepatocyte growth factor and its variant with a deletion of five amino acids are distinguishable in their biological activity and tertiary structure," *Biochem. Biophys. Res. Commun.* 200:808-815, Academic Press, United States (1994).

Taniyama et al., "Therapeutic angiogenesis induced by human hepatocyte growth factor gene in rat and rabbit hindlimb ischemia models: preclinical study for treatment of peripheral arterial disease" *Gene Therapy* 8:181-189, Nature Publishing Group (2001).

Yang, et al., "Sustained Expression of Naked Plasmid DNA Encoding Hepatocyte Growth Factor in Mice Promotes Liver and Overall Body Growth," Hepatology 33:848-859, American Assoc. for the Study of Liver Disease (2001).

Office Action for U.S. Appl. No. 12/421,425, mailed Aug. 19, 2010.
Office Action for U.S. Appl. No. 12/421,425, mailed Dec. 17, 2010.

\* cited by examiner

SEQUENCE LISTING

<160> NUMBER OF SEQ ID NOS: 14

<210> SEQ ID NO 1
<211> LENGTH: 2187
<212> TYPE: DNA
<213> ORGANISM: Homo sapiens

<400> SEQUENCE: 1

```
atgtgggtga ccaaactcct gccagccctg ctgctgcagc atgtcctcct gcatctcctc      60
ctgctcccca tcgccatccc ctatgcagag ggacaaagga aaagaagaaa tacaattcat     120
gaattcaaaa aatcagcaaa gactacccta atcaaaatag atccagcact gaagataaaa     180
accaaaaaag tgaatactgc agaccaatgt gctaatagat gtactaggaa taaaggactt     240
ccattcactt gcaaggcttt tgtttttgat aaagcaagaa acaatgcct ctggttcccc      300 ttcaatagca tgtcaagtgg agtgaaaaaa gaatttggcc atgaatttga cctctatgaa     360
aacaaagact acattagaaa ctgcatcatt ggtaaaggac gcagctacaa gggaacagta     420
tctatcacta agagtggcat caaatgtcag ccctggagtt ccatgatacc acacgaacac     480 agcttttttgc cttcgagcta tcggggtaaa gacctacagg aaaactactg tcgaaatcct     540 cgagggaag aagggggacc ctggtgtttc acaagcaatc cagaggtacg ctacgaagtc      600
tgtgacattc ctcagtgttc agaagttgaa tgcatgacct gcaatgggga gagttatcga     660
ggtctcatgg atcatacaga atcaggcaag atttgtcagc gctgggatca tcagacacca     720
caccggcaca aattcttgcc tgaaagatat cccgacaagg gctttgatga taattattgc     780
cgcaatcccg atggccagcc gaggccatgg tgctatactc ttgaccctca cacccgctgg     840
gagtactgtg caattaaaaac atgcgctgac aatactatga atgacactga tgttcctttg     900
gaaacaactg aatgcatcca aggtcaagga gaaggctaca gggcactgt caataccatt      960 tggaatggaa ttccatgtca gcgttgggat tctcagtatc ctcacgagca tgacatgact    1020
cctgaaaatt tcaagtgcaa ggacctacga gaaaattact gccgaaatcc agatgggtct    1080
gaatcaccct ggtgttttac cactgatcca aacatccgag ttggctactg ctcccaaatt    1140
ccaaactgtg atatgtcaca tggacaagat tgttatcgtg ggaatggcaa aaattatatg    1200
ggcaacttat cccaaacaag atctggacta acatgttcaa tgtgggacaa gaacatggaa    1260
gacttacatc gtcatatctt ctgggaacca gatgcaagta agctgaatga gaattactgc    1320
cgaaatccag atgatgatgc tcatggaccc tggtgctaca cgggaaatcc actcattcct    1380
tgggattatt gccctatttc tcgttgtgaa ggtgatacca cacctacaat agtcaattta    1440
gaccatcccg taatatcttg tgccaaaacg aaacaattgc gagttgtaaa tgggattcca    1500
acacgaacaa acataggatg gatggttagt ttgagataca gaaataaaca tatctgcgga    1560
ggatcattga taaaggagag ttgggttctt actgcacgac agtgtttccc ttctcgagac    1620
ttgaaagatt atgaagcttg gcttggaatt catgatgtcc acggaagagg agatgagaaa    1680
tgcaaacagg ttctcaatgt ttcccagctg gtatatggcc ctgaaggatc agatctggtt    1740
ttaatgaagc ttgccaggcc tgctgtcctg gatgattttg ttagtacgat tgatttacct    1800
aattatggat gcacaattcc tgaaaagacc agttgcagtg tttatggctg gggctacact    1860
ggattgatca actatgatgg cctattacga gtggcacatc tctatataat gggaaatgag    1920
aaatgcagcc agcatcatcg agggaaggtg actctgaatg agtctgaaat atgtgctggg    1980
gctgaaaaga ttggatcagg accatgtgag ggggattatg gtggcccact tgtttgtgag    2040
```

```
caacataaaa tgagaatggt tcttggtgtc attgttcctg gtcgtggatg tgccattcca   2100
aatcgtcctg gtattttgt ccgagtagca tattatgcaa aatggataca caaaattatt   2160
ttaacatata aggtaccaca gtcatag                                       2187
```

<210> SEQ ID NO 2
<211> LENGTH: 728
<212> TYPE: PRT
<213> ORGANISM: Homo sapiens

<400> SEQUENCE: 2

```
Met Trp Val Thr Lys Leu Leu Pro Ala Leu Leu Leu Gln His Val Leu
  1               5                  10                  15

Leu His Leu Leu Leu Pro Ile Ala Ile Pro Tyr Ala Glu Gly Gln
                 20                  25                  30

Arg Lys Arg Arg Asn Thr Ile His Glu Phe Lys Lys Ser Ala Lys Thr
             35                  40                  45

Thr Leu Ile Lys Ile Asp Pro Ala Leu Lys Ile Lys Thr Lys Lys Val
 50                  55                  60

Asn Thr Ala Asp Gln Cys Ala Asn Arg Cys Thr Arg Asn Lys Gly Leu
 65                  70                  75                  80

Pro Phe Thr Cys Lys Ala Phe Val Phe Asp Lys Ala Arg Lys Gln Cys
                 85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350
```

Tyr Cys Arg Asn Pro Asp Gly Ser Glu Ser Pro Trp Cys Phe Thr Thr
            355                 360                 365

Asp Pro Asn Ile Arg Val Gly Tyr Cys Ser Gln Ile Pro Asn Cys Asp
370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 3
<211> LENGTH: 723
<212> TYPE: PRT
<213> ORGANISM: Homo sapiens

<400> SEQUENCE: 3

-continued

```
Met Trp Val Thr Lys Leu Leu Pro Ala Leu Leu Gln His Val Leu
 1               5                  10                 15

Leu His Leu Leu Leu Leu Pro Ile Ala Ile Pro Tyr Ala Glu Gly Gln
                20              25                 30

Arg Lys Arg Arg Asn Thr Ile His Glu Phe Lys Lys Ser Ala Lys Thr
            35                  40                 45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
 65                 70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
                100                 105                110

Gly His Glu Phe Asp Leu Tyr Glu Asn Lys Asp Tyr Ile Arg Asn Cys
            115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Tyr Arg Gly Lys Asp Leu Gln Glu Asn Tyr Cys Arg Asn Pro Arg
                165                 170                 175

Gly Glu Glu Gly Gly Pro Trp Cys Phe Thr Ser Asn Pro Glu Val Arg
            180                 185                 190

Tyr Glu Val Cys Asp Ile Pro Gln Cys Ser Glu Val Glu Cys Met Thr
        195                 200                 205

Cys Asn Gly Glu Ser Tyr Arg Gly Leu Met Asp His Thr Glu Ser Gly
210                 215                 220

Lys Ile Cys Gln Arg Trp Asp His Gln Thr Pro His Arg His Lys Phe
225                 230                 235                 240

Leu Pro Glu Arg Tyr Pro Asp Lys Gly Phe Asp Asp Asn Tyr Cys Arg
                245                 250                 255

Asn Pro Asp Gly Gln Pro Arg Pro Trp Cys Tyr Thr Leu Asp Pro His
            260                 265                 270

Thr Arg Trp Glu Tyr Cys Ala Ile Lys Thr Cys Ala Asp Asn Thr Met
    275                 280                 285

Asn Asp Thr Asp Val Pro Leu Glu Thr Thr Glu Cys Ile Gln Gly Gln
290                 295                 300

Gly Glu Gly Tyr Arg Gly Thr Val Asn Thr Ile Trp Asn Gly Ile Pro
305                 310                 315                 320

Cys Gln Arg Trp Asp Ser Gln Tyr Pro His Glu His Asp Met Thr Pro
                325                 330                 335

Glu Asn Phe Lys Cys Lys Asp Leu Arg Glu Asn Tyr Cys Arg Asn Pro
            340                 345                 350

Asp Gly Ser Glu Ser Pro Trp Cys Phe Thr Thr Asp Pro Asn Ile Arg
        355                 360                 365

Val Gly Tyr Cys Ser Gln Ile Pro Asn Cys Asp Met Ser His Gly Gln
    370                 375                 380

Asp Cys Tyr Arg Gly Asn Gly Lys Asn Tyr Met Gly Asn Leu Ser Gln
385                 390                 395                 400

Thr Arg Ser Gly Leu Thr Cys Ser Met Trp Asp Lys Asn Met Glu Asp
                405                 410                 415

Leu His Arg His Ile Phe Trp Glu Pro Asp Ala Ser Lys Leu Asn Glu
            420                 425                 430
```

```
Asn Tyr Cys Arg Asn Pro Asp Asp Ala His Gly Pro Trp Cys Tyr
            435                 440                 445

Thr Gly Asn Pro Leu Ile Pro Trp Asp Tyr Cys Pro Ile Ser Arg Cys
        450                 455                 460

Glu Gly Asp Thr Thr Pro Thr Ile Val Asn Leu Asp His Pro Val Ile
465                 470                 475                 480

Ser Cys Ala Lys Thr Lys Gln Leu Arg Val Val Asn Gly Ile Pro Thr
                485                 490                 495

Arg Thr Asn Ile Gly Trp Met Val Ser Leu Arg Tyr Arg Asn Lys His
                500                 505                 510

Ile Cys Gly Gly Ser Leu Ile Lys Glu Ser Trp Val Leu Thr Ala Arg
            515                 520                 525

Gln Cys Phe Pro Ser Arg Asp Leu Lys Asp Tyr Glu Ala Trp Leu Gly
        530                 535                 540

Ile His Asp Val His Gly Arg Gly Asp Glu Lys Cys Lys Gln Val Leu
545                 550                 555                 560

Asn Val Ser Gln Leu Val Tyr Gly Pro Glu Gly Ser Asp Leu Val Leu
                565                 570                 575

Met Lys Leu Ala Arg Pro Ala Val Leu Asp Asp Phe Val Ser Thr Ile
                580                 585                 590

Asp Leu Pro Asn Tyr Gly Cys Thr Ile Pro Glu Lys Thr Ser Cys Ser
            595                 600                 605

Val Tyr Gly Trp Gly Tyr Thr Gly Leu Ile Asn Tyr Asp Gly Leu Leu
        610                 615                 620

Arg Val Ala His Leu Tyr Ile Met Gly Asn Glu Lys Cys Ser Gln His
625                 630                 635                 640

His Arg Gly Lys Val Thr Leu Asn Glu Ser Glu Ile Cys Ala Gly Ala
                645                 650                 655

Glu Lys Ile Gly Ser Gly Pro Cys Glu Gly Asp Tyr Gly Gly Pro Leu
            660                 665                 670

Val Cys Glu Gln His Lys Met Arg Met Val Leu Gly Val Ile Val Pro
        675                 680                 685

Gly Arg Gly Cys Ala Ile Pro Asn Arg Pro Gly Ile Phe Val Arg Val
690                 695                 700

Ala Tyr Tyr Ala Lys Trp Ile His Lys Ile Ile Leu Thr Tyr Lys Val
705                 710                 715                 720

Pro Gln Ser

<210> SEQ ID NO 4
<211> LENGTH: 207
<212> TYPE: PRT
<213> ORGANISM: Homo sapiens

<400> SEQUENCE: 4

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80
```

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser
        195                 200                 205

<210> SEQ ID NO 5
<211> LENGTH: 290
<212> TYPE: PRT
<213> ORGANISM: Homo sapiens

<400> SEQUENCE: 5

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

```
Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
            275                 280                 285

Glu Thr
    290

<210> SEQ ID NO 6
<211> LENGTH: 470
<212> TYPE: PRT
<213> ORGANISM: Homo sapiens

<400> SEQUENCE: 6

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335
```

```
His Asp Met Thr Pro Glu Asn Phe Lys Cys Lys Asp Leu Arg Glu Asn
              340                 345                 350
Tyr Cys Arg Asn Pro Asp Gly Ser Glu Ser Pro Trp Cys Phe Thr Thr
          355                 360                 365
Asp Pro Asn Ile Arg Val Gly Tyr Cys Ser Gln Ile Pro Asn Cys Asp
    370                 375                 380
Met Ser His Gly Gln Asp Cys Tyr Arg Gly Asn Gly Lys Asn Tyr Met
385                 390                 395                 400
Gly Asn Leu Ser Gln Thr Arg Ser Gly Leu Thr Cys Ser Met Trp Asp
              405                 410                 415
Lys Asn Met Glu Asp Leu His Arg His Ile Phe Trp Glu Pro Asp Ala
          420                 425                 430
Ser Lys Leu Asn Glu Asn Tyr Cys Arg Asn Pro Asp Asp Asp Ala His
    435                 440                 445
Gly Pro Trp Cys Tyr Thr Gly Asn Pro Leu Ile Pro Trp Asp Tyr Cys
    450                 455                 460
Pro Ile Ser Arg Cys Glu
465                 470

<210> SEQ ID NO 7
<211> LENGTH: 7113
<212> TYPE: DNA
<213> ORGANISM: Artificial Sequence
<220> FEATURE:
<223> OTHER INFORMATION: synthetic hepatocyte growth factor hybrid

<400> SEQUENCE: 7
atgtgggtga ccaaactcct gccagccctg ctgctgcagc atgtcctcct gcatctcctc      60
ctgctcccca tcgccatccc ctatgcagag ggacaaagga aagaagaaa tacaattcat     120
gaattcaaaa atcagcaaa gactacccta atcaaaatag atccagcact gaagataaaa     180
accaaaaaag tgaatactgc agaccaatgt gctaatagat gtactaggaa taaaggactt     240
ccattcactt gcaaggcttt tgttttttgat aaagcaagaa acaatgcct ctggttcccc     300
ttcaatagca tgtcaagtgg agtgaaaaaa gaatttggcc atgaatttga cctctatgaa     360
aacaaagact acattagaaa ctgcatcatt ggtaaaggac gcagctacaa gggaacagta     420
tctatcacta gagtggcat caaatgtcag ccctggagtt ccatgatacc acacgaacac     480
aggtaagaac agtatgaaga aaagagatga agcctctgtc ttttttacat gttaacagtc     540
tcatattagt ccttcagaat aattctacaa tcctaaaata acttagccaa cttgctgaat     600
tgtattacgg caaggtttat atgaattcat gactgatatt tagcaaatga ttaattaata     660
tgttaataaa atgtagccaa acaatatct taccttaatg cctcaatttg tagatctcgg     720
tatttgtgaa ataataacgt aaacttcgtt taaaaggatt cttcttcctg tctttgagaa     780
agtacggcac tgtgcagggg gagaggttga ttgtgaaaaa tcagaggtag atgagaatct     840
tactgagggc tgagggttct ttaaccttgg tggatctcaa cattggttgc acattaaaat     900
cacctgctgc aagcccttga cgaatcttac ttagaagatg acaacacaga acaattaaat     960
cagaatctct ggggagaata gggcaccagt atttttgag ctcccaccat gattccaaag    1020
tgcagccaaa tttgagaacc actgctaaaa gctcaagctt cagattgacc agcttttcca    1080
tctcacctat cgcctaaaga ccaaattgga taaatgtgtt cattacgaca gatgggtact    1140
atttaaagat gagtaaacac aatatactta ggctcgtcag actgagagtt ttaatcatca    1200
ctgaggaaaa acatagatat ctaatactga ctggagtatt agtcaaggct tatttcacac    1260
acaatttat cagaaaccaa agtagtttaa acagctctc cccttattag taatgcattg    1320
```

```
gagggtttac tttaccatgt accttgctga gcactgtacc ttgttaatct catttacttg    1380
taatgagaac cacacagcgg gtagttttat tggttctatt ttacctacat gacaaaactg    1440
aagcataaaa acacttagta agttttcagt gtcatgcaca actaggaagt gacatggcca    1500
gaatataagc ccagtcacca tcactctata acctgcgctt ttaacaactt cagggcatga    1560
cacatttggc cggtcagtag aacccatgct gtgatttgtt tttgcagtgg tggtgatgac    1620
tgccttgttg aatccacttt ttattctatt ccattttggg gacacaattc tgcaagatga    1680
ttcttcatta ggaaacagag atgagttatt gaccaacaca gaaagaaaaa gagtttgttg    1740
ctccacactg ggattaaacc tatgatcttg gcctaattaa cactagctag taagtgtcca    1800
agctgatcat ctctacaaca tttcaataac agaaaacaac aatttcaaa attagttact    1860 tacaattatg tagaaatgcc tctaaaacac agtattttcc ttatattaca aaacaaaaa    1920 ttataattgg ttttgtcctc ttttgagagt ttgcatggtg ttactccctg catagtgaag    1980
aaaacatttt atttaagtag atggatctaa gttttcatg aacaaggaa tgacatttga    2040 aatcaatcct accctagtcc aggagaatgc attagattaa cctagtagag gtcttatttc    2100
accctgagtt ttctatgatc gtgattctct gctggaggag taattgtgaa atagatctct    2160
ctgggaactg gcttcctagt ccaatcagct cttttaccaa tgaacacttc cttgtgatat    2220
agatgtttat ggccgagagg atccagtata ttaataaaat cccttttgt attcaatgag    2280 ggaaacacat aattttcatc aattagcagc ttattggaat atctgcatga tggtttaaca    2340
cttttaagtg ttgactaaag attaatttta cagaaaatag aaaagaaat atgtttctgt    2400 ctggaggaat gatttattgt tgacccctaa attgaaatat tttactagtg gcttaatgga    2460
aagatgatga aagatgatga aattaatgta gaagcttaac tagaaaatca ggtgacctga    2520
tatctacatc tgtatccttc attggccacc cagcattcat taatgaatca gatgatggaa    2580
tagatcaagt ttcctaggaa cacagtgaat attaaaagaa aacaaaggga gcctagcacc    2640
tagaagacct agtttatatt tcaaagtata tttggatgta acccaatttt aaacatttcc    2700
tcacttgtct ctcttaaagc cttgccaaca gcaaggacag agaaccaaaa atagtgtata    2760
tatgaataaa tgcttattac agaatctgct gactggcaca tgctttgtgt gtaatgggtt    2820
ctcataaaca cttgttgaat gaacacacat aagtgaaaga gcatggctag gcttcatccc    2880
ttggtcaaat atggggtgct aaagaaaagc aggggaaata cattgggaca ctaacaaaaa    2940
aaaacagtta atttaggtaa aagataaaat acaccacaga atgaagaaaa gagatgaccc    3000
agactgctct ttaaccttca tgtcctagag aggttttga tatgaattgc attcagaatt    3060
gtggaaagga gcccatcttt tctcttcatt ttgatttat taactccaat gggggaattt    3120
tattcgtgtt ttggccatat ctactttga tttctacatt attctctctt cctttctacc    3180
tgtatttgtc ctaataaatt gttgacttat taattcacta cttcctcaca gcttttttt    3240 ggctttacaa atccactgga aaggtatatg ggtgtatcac tttgtgtatt tcggtgtgca    3300
tgtgtagagg ggacaaaaat cctctctcaa actataaata ttgagtatt gtgtattgaa    3360 catttgctat aactactagg tttcttaaat aatcttaata tataaaatga tatagaaaaa    3420
gggaaattat agttcgtatt attcatctaa gtgaagagat taaacccag ggagtaaata    3480 aattgtctaa ggactaaggt tgtatactat ttaggtgata gatatgggc aaccgtatgg    3540 gtttatgat taacaaataa acttctcacc actctaccat atcaactttt ccataaaaga    3600
gagctatagt attctttgct taaataaatt tgattagtgc atgacttctt gaaaacatat    3660
aaagcaaaag tcacatttga ttctatcaga aaagtgagta agccatggcc caaacaaaag    3720
```

```
atgcattaaa atattctgga atgatggagc taaaagtaag aaaaatgact ttttaaaaaa   3780
gtttactgtt aggaattgtg aaattatgct gaattttagt tgcattataa ttttgtcag    3840 tcatacggtc tgacaacctg tcttatttct atttccccat atgaggaatg ctagttaagt   3900
atggatatta actattacta cttagatgca ttgaagttgc ataatatgga taatacttca   3960
ctggttccct gaaatgtttt agttagtaat aagtctctta cactatttgt tttgtccaat   4020
aatttatatt ttctgaagac ttaactctag aatacactca tgtcaaaatg aaagaatttc   4080
attgcaaaat attgcttggt acatgacgca tacctgtatt tgttttgtgt cacaacatga   4140
aaaatgatgg tttattagaa gtttcattgg gtaggaaaca catttgaatg gtatttacta   4200
agatactaaa atccttggac ttcactctaa ttttagtgcc atttagaact caaggtctca   4260
gtaaaagtag aaataaagcc tgttaacaaa acacaagctg aatattaaaa atgtaactgg   4320
attttcaaag aaatgtttac tggtattacc tgtagatgta tattctttat tatgatcttt   4380
tgtgtaaagt ctggcagaca aatgcaatat ctaattgttg agtccaatat cacaagcagt   4440 acaaagtat aaaaaagact tggccttttc taatgtgtta aaatacttta tgctggtaat    4500
aacactaaga gtagggcact agaaatttta agtgaagata atgtgttgca gttactgcac   4560
tcaatggctt actattataa accaaaactg ggatcactaa gctccagtca gtcaaaatga   4620
tcaaaattat tgaagagaat aagcaattct gttctttatt aggacacagt agatacagac   4680
tacaaagtgg agtgtgctta ataagaggta gcatttgtta agtgtcaatt actctattat   4740
cccttggagc ttctcaaaat aaccatataa ggtgtaagat gttaaaggtt atggttacac   4800
tcagtgcaca ggtaagctaa taggctgaga gaagctaaat tacttactgg ggtctcacag   4860
taagaaagtg agctgaagtt tcagcccaga tttaactgga ttctgggctc tttattcatg   4920
ttacttcatg aatctgtttc tcaattgtgc agaaaaaagg gggctattta taagaaaagc   4980
aataaacaaa caagtaatga tctcaaataa gtaatgcaag aaatagtgag atttcaaaat   5040
cagtggcagc gatttctcag ttctgtccta agtggccttg ctcaatcacc tgctatcttt   5100
tagtggagct ttgaaattat gtttcagaca acttcgattc agttctagaa tgtttgactc   5160
agcaaattca caggctcatc tttctaactt gatggtgaat atggaaattc agctaaatgg   5220
atgttaataa aattcaaacg ttttaaggac agatgaaaat gacagaattt taaggtaaaa   5280
tatatgaagg aatataagat aaaggatttt tctaccttca gcaaaaacat acccactaat   5340
tagtaaaatt aataggcaaa aaaaagttgc atgctcttat actgtaatga ttatcatttt   5400
aaaactagct ttttgccttc gagctatcgg ggtaaagacc tacaggaaaa ctactgtcga   5460
aatcctcgag gggaagaagg gggaccctgg tgtttcacaa gcaatccaga ggtacgctac   5520
gaagtctgtg acattcctca gtgttcagaa gttgaatgca tgacctgcaa tggggagagt   5580
tatcgaggtc tcatggatca tacagaatca ggcaagattt gtcagcgctg ggatcatcag   5640
acaccacacc ggcacaaatt cttgcctgaa agatatcccg acaagggctt tgatgataat   5700
tattgccgca atcccgatgg ccagccgagg ccatggtgct atactcttga ccctcacacc   5760
cgctgggagt actgtgcaat taaaacatgc gctgacaata ctatgaatga cactgatgtt   5820
cctttggaaa caactgaatg catccaaggt caaggagaag gctacagggg cactgtcaat   5880
accatttgga atggaattcc atgtcagcgt tgggattctc agtatcctca cgagcatgac   5940
atgactcctg aaaatttcaa gtgcaaggac ctacgagaaa attactgccg aaatccagat   6000
gggtctgaat caccctggtg ttttaccact gatccaaaca tccgagttgg ctactgctcc   6060
caaattccaa actgtgatat gtcacatgga caagattgtt atcgtgggaa tggcaaaaat   6120
```

| | |
|---|---|
| tatatgggca acttatccca aacaagatct ggactaacat gttcaatgtg ggacaagaac | 6180 |
| atggaagact tacatcgtca tatcttctgg gaaccagatg caagtaagct gaatgagaat | 6240 |
| tactgccgaa atccagatga tgatgctcat ggaccctggt gctacacggg aaatccactc | 6300 |
| attccttggg attattgccc tatttctcgt tgtgaaggtg ataccacacc tacaatagtc | 6360 |
| aatttagacc atcccgtaat atcttgtgcc aaaacgaaac aattgcgagt tgtaaatggg | 6420 |
| attccaacac gaacaaacat aggatggatg gttagtttga gatacagaaa taaacatatc | 6480 |
| tgcggaggat cattgataaa ggagagttgg gttcttactg cacgacagtg tttcccttct | 6540 |
| cgagacttga agattatga agcttggctt ggaattcatg atgtccacgg aagaggagat | 6600 |
| gagaaatgca acaggttct caatgttttcc cagctggtat atggccctga aggatcagat | 6660 |
| ctggttttaa tgaagcttgc caggcctgct gtcctggatg attttgttag tacgattgat | 6720 |
| ttacctaatt atggatgcac aattcctgaa aagaccagtt gcagtgttta tggctggggc | 6780 |
| tacactggat tgatcaacta tgatggccta ttacgagtgg cacatctcta tataatggga | 6840 |
| aatgagaaat gcagccagca tcatcgaggg aaggtgactc tgaatgagtc tgaaatatgt | 6900 |
| gctgggctg aaaagattgg atcaggacca tgtgaggggg attatggtgg cccacttgtt | 6960 |
| tgtgagcaac ataaaatgag aatggttctt ggtgtcattg ttcctggtcg tggatgtgcc | 7020 |
| attccaaatc gtcctggtat ttttgtccga gtagcatatt atgcaaaatg gatacacaaa | 7080 |
| attatttta catataaggt accacagtca tag | 7113 |

<210> SEQ ID NO 8
<211> LENGTH: 4679
<212> TYPE: DNA
<213> ORGANISM: Artificial Sequence
<220> FEATURE:
<223> OTHER INFORMATION: Synthetic HGF-X6 gene

<400> SEQUENCE: 8

| | |
|---|---|
| atgtgggtga ccaaactcct gccagccctg ctgctgcagc atgtcctcct gcatctcctc | 60 |
| ctgctcccca tcgccatccc ctatgcagag ggacaaagga aaagaagaaa tacaattcat | 120 |
| gaattcaaaa aatcagcaaa gactacccta atcaaaatag atccagcact gaagataaaa | 180 |
| accaaaaaag tgaatactgc agaccaatgt gctaatagat gtactaggaa taaaggactt | 240 |
| ccattcactt gcaaggcttt tgttttttgat aaagcaagaa acaatgcct ctggttcccc | 300 |
| ttcaatagca tgtcaagtgg agtgaaaaaa gaatttggcc atgaatttga cctctatgaa | 360 |
| aacaaagact acattagaaa ctgcatcatc ggtaaaggac gcagctacaa gggaacagta | 420 |
| tctatcacta gagtggcat caaatgtcag ccctggagtt ccatgatacc acacgaacac | 480 |
| aggtaagaac agtatgaaga aagagatga agcctctgtc tttttttacat gttaacagtc | 540 |
| tcatattagt ccttcagaat aattctacaa tcctaaaata acttagccaa cttgctgaat | 600 |
| tgtattacgg caaggtttat atgaattcat gactgatatt tagcaaatga ttaattaata | 660 |
| tgttaataaa atgtagccaa acaatatct taccttaatg cctcaatttg tagatctcgg | 720 |
| tatttgtgga tcccttcctt tctacctgta tttgtcctaa taaattgttg acttattaat | 780 |
| tcactacttc ctcacagctt ttttttggct ttacaaatcc actggaaagg tatatgggtg | 840 |
| tatcactttg tgtatttcgg tgtgcatgtg tagagggac aaaaatcctc tctcaaacta | 900 |
| taaatattga gtatttgtgt attgaacatt tgctataact actaggtttc ttaaataatc | 960 |
| ttaatatata aaatgatata gaaaagggaa attatagtt cgtattattc atctcaagtga | 1020 |
| agagattaaa acccagggag taaataaatt gtctaaggac taaggttgta tactatttag | 1080 |

| | |
|---|---|
| gtgatagata tggggcaacc gtatgggttt tatgattaac aaataaactt ctcaccactc | 1140 |
| taccatatca acttttccat aaaagagagc tatagtattc tttgcttaaa taaatttgat | 1200 |
| tagtgcatga cttcttgaaa acatataaag caaaagtcac atttgattct atcagaaaag | 1260 |
| tgagtaagcc atggcccaaa caaaagatgc attaaaatat tctggaatga tggagctaaa | 1320 |
| agtaagaaaa atgactttt aaaaaagttt actgttagga attgtgaaat tatgctgaat | 1380 |
| tttagttgca ttataatttt tgtcagtcat acggtctgac aacctgtctt atttctattt | 1440 |
| ccccatatga ggaatgctag ttaagtatgg atattaacta ttactactta gatgcattga | 1500 |
| agttgcataa tatggataat acttcactgg ttccctgaaa atgtttagtt agtaataagt | 1560 |
| ctcttacact atttgttttg tccaataatt tatattttct gaagacttaa ctctagaata | 1620 |
| cactcatgtc aaaatgaaag aatttcattg caaatatttg cttggtacat gacgcatacc | 1680 |
| tgtatttgtt ttgtgtcaca acatgaaaaa tgatggttta ttagaagttt cattgggtag | 1740 |
| gaaacacatt tgaatggtat ttactaagat actaaaatcc ttggacttca ctctaatttt | 1800 |
| agtgccattt agaactcaag gtctcagtaa aagtagaaat aaagcctgtt aacaaaacac | 1860 |
| aagctgaata ttaaaaatgt aactggattt tcaaagaaat gtttactggt attacctgta | 1920 |
| gatgtatatt ctttattatg atcttttgtg taaagtctgg cagacaaatg caatatctaa | 1980 |
| ttgttgagtc caatatcaca agcagtacaa agtataaaa aagacttggc cttttctaat | 2040 |
| gtgttaaaat actttatgct ggtaataaca ctaagagtag ggcactagaa attttaagtg | 2100 |
| aagataatgt gttgcagtta ctgcactcaa tggcttacta ttataaacca aaactgggat | 2160 |
| cactaagctc cagtcagtca aaatgatcaa aattattgaa gagaataagc aattctgttc | 2220 |
| tttattagga cacagtagat acagactaca aagtggagtg tgcttaataa gaggtagcat | 2280 |
| ttgttaagtg tcaattactc tattatccct tggagcttct caaaataacc atataaggtg | 2340 |
| taagatgtta aaggttatgg ttacactcag tgcacaggta agctaatagg ctgagagaag | 2400 |
| ctaaattact tactggggtc tcacagtaag aaagtgagct gaagtttcag cccagattta | 2460 |
| actggattct gggctcttta ttcatgttac ttcatgaatc tgtttctcaa ttgtgcagaa | 2520 |
| aaaaggggc tatttataag aaaagcaata aacaaacaag taatgatctc aaataagtaa | 2580 |
| tgcaagaaat agtgagattt caaaatcagt ggcagcgatt tctcagttct gtcctaagtg | 2640 |
| gccttgctca atcacctgct atcttttagt ggagctttga aattatgttt cagacaactt | 2700 |
| cgattcagtt ctagaatgtt tgactcagca aattcacagg ctcatctttc taacttgatg | 2760 |
| gtgaatatgg aaattcagct aaatggatgt taataaaatt caaacgtttt aaggacagat | 2820 |
| gaaaatgaca gaattttaag gtaaaatata tgaaggaata taagataaag gattttcta | 2880 |
| ccttcagcaa aaacataccc actaattagt aaaattaata ggcaaaaaaa agttgcatgc | 2940 |
| tcttatactg taatgattat cattttaaaa ctagcttttt gccttcgagc tatcggggta | 3000 |
| aagacctaca ggaaaactac tgtcgaaatc ctcgagggga agaaggggga ccctggtgtt | 3060 |
| tcacaagcaa tccagaggta cgctacgaag tctgtgacat tcctcagtgt tcagaagttg | 3120 |
| aatgcatgac ctgcaatggg gagagttatc gaggtctcat ggatcataca gaatcaggca | 3180 |
| agatttgtca gcgctgggat catcagacac cacaccggca caaattcttg cctgaaagat | 3240 |
| atcccgacaa gggctttgat gataattatt gccgcaatcc cgatggccag ccgaggccat | 3300 |
| ggtgctatac tcttgaccct cacacccgct gggagtactg tgcaattaaa acatgcgctg | 3360 |
| acaatactat gaatgacact gatgttcctt tggaaacaac tgaatgcatc caaggtcaag | 3420 |
| gagaaggcta caggggcact gtcaatacca tttggaatgg aattccatgt cagcgttggg | 3480 |

```
attctcagta tcctcacgag catgacatga ctcctgaaaa tttcaagtgc aaggacctac    3540
gagaaaatta ctgccgaaat ccagatgggt ctgaatcacc ctggtgtttt accactgatc    3600
caaacatccg agttggctac tgctcccaaa ttccaaactg tgatatgtca catggacaag    3660
attgttatcg tgggaatggc aaaaattata tgggcaactt atcccaaaca agatctggac    3720
taacatgttc aatgtgggac aagaacatgg aagacttaca tcgtcatatc ttctgggaac    3780
cagatgcaag taagctgaat gagaattact gccgaaatcc agatgatgat gctcatggac    3840
cctggtgcta cacgggaaat ccactcattc cttgggatta ttgccctatt tctcgttgtg    3900
aaggtgatac cacacctaca atagtcaatt tagaccatcc cgtaatatct tgtgccaaaa    3960
cgaaacaatt gcgagttgta atgggattcc aacacgaac aaacatagga tggatggtta    4020
gtttgagata cagaaataaa catatctgcg gaggatcatt gataaaggag agttgggttc    4080
ttactgcacg acagtgtttc ccttctcgag acttgaaaga ttatgaagct ggcttggaa    4140 ttcatgatgt ccacggaaga ggagatgaga atgcaaaca ggttctcaat gtttcccagc    4200
tggtatatgg ccctgaagga tcagatctgg ttttaatgaa gcttgccagg cctgctgtcc    4260
tggatgattt tgttagtacg attgatttac ctaattatgg atgcacaatt cctgaaaaga    4320
ccagttgcag tgtttatggc tggggctaca ctggattgat caactatgat ggcctattac    4380
gagtggcaca tctctatata tgggaaatg agaaatgcag ccagcatcat cgagggaagg    4440
tgactctgaa tgagtctgaa atatgtgctg gggctgaaaa gattggatca ggaccatgtg    4500
agggggatta tggtggccca cttgtttgtg agcaacataa aatgagaatg gttcttggtg    4560
tcattgttcc tggtcgtgga tgtgccattc caaatcgtcc tggtattttt gtccgagtag    4620
catattatgc aaaatggata cacaaaatta ttttaacata aaggtaccca cagtcatag    4679

<210> SEQ ID NO 9
<211> LENGTH: 3679
<212> TYPE: DNA
<213> ORGANISM: Artificial Sequence
<220> FEATURE:
<223> OTHER INFORMATION: Synthetic HGF-X7 gene

<400> SEQUENCE: 9
atgtgggtga ccaaactcct gccagccctg ctgctgcagc atgtcctcct gcatctcctc      60
ctgctcccca tcgccatccc ctatgcagag ggacaaagga aagaagaaa tacaattcat     120 gaattcaaaa aatcagcaaa gactacccta atcaaaatag atccagcact gaagataaaa     180
accaaaaaag tgaatactgc agaccaatgt gctaatagat gtactaggaa taaaggactt     240
ccattcactt gcaaggcttt tgttttttgat aaagcaagaa acaatgcct ctggttcccc     300 ttcaatagca tgtcaagtgg agtgaaaaaa gaatttggcc atgaatttga cctctatgaa     360
aacaaagact acattagaaa ctgcatcatc ggtaaaggac gcagctacaa gggaacagta     420
tctatcacta gagtggcat caaatgtcag ccctggagtt ccatgatacc acacgaacac     480
aggtaagaac agtatgaaga aaagagatga agccctctgt cttttttacat gttaacagtc     540 tcatattagt ccttcagaat aattctacaa tcctaaaata acttagccaa cttgctgaat     600
tgtattacgg caaggtttat atgaattcat gactgatatt tagcaaatga ttaattaata     660
tgttaataaa atgtagccaa acaatatct taccttaatg cctcaatttg tagatctcgg     720
tatttgtgga tcctgggtag gaaacacatt tgaatggtat ttactaagat actaaaatcc     780
ttggacttca ctctaatttt agtgccattt agaactcaag gtctcagtaa agtagaaat    840 aaagcctgtt aacaaaacac aagctgaata ttaaaaatgt aactggatt caaagaaat    900
```

```
gtttactggt attacctgta gatgtatatt ctttattatg atcttttgtg taaagtctgg    960
cagacaaatg caatatctaa ttgttgagtc caatatcaca agcagtacaa agtataaaa    1020 aagacttggc cttttctaat gtgttaaaat actttatgct ggtaataaca ctaagagtag   1080
ggcactagaa attttaagtg aagataatgt gttgcagtta ctgcactcaa tggcttacta   1140
ttataaacca aaactgggat cactaagctc cagtcagtca aaatgatcaa aattattgaa   1200
gagaataagc aattctgttc tttattagga cacagtagat acagactaca aagtggagtg   1260
tgcttaataa gaggtagcat ttgttaagtg tcaattactc tattatccct tggagcttct   1320
caaaataacc atataaggtg taagatgtta aaggttatgg ttacactcag tgcacaggta   1380
agctaatagg ctgagagaag ctaaattact tactggggtc tcacagtaag aaagtgagct   1440
gaagtttcag cccagattta actggattct gggctcttta ttcatgttac ttcatgaatc   1500
tgtttctcaa ttgtgcagaa aaagggggc tatttataag aaaagcaata aacaaacaag    1560
taatgatctc aaataagtaa tgcaagaaat agtgagattt caaaatcagt ggcagcgatt   1620
tctcagttct gtcctaagtg gccttgctca atcacctgct atcttttagt ggagctttga   1680
aattatgttt cagacaactt cgattcagtt ctagaatgtt tgactcagca aattcacagg   1740
ctcatctttc taacttgatg gtgaatatgg aaattcagct aaatggatgt taataaaatt   1800
caaacgtttt aaggacagat gaaaatgaca gaattttaag gtaaaatata tgaaggaata   1860
taagataaag gattttttcta ccttcagcaa aaacatacccc actaattagt aaaattaata  1920
ggcaaaaaaa agttgcatgc tcttatactg taatgattat cattttaaaa ctagcttttt   1980
gccttcgagc tatcggggta aagacctaca ggaaaactac tgtcgaaatc ctcgagggga   2040 agaagggga ccctggtgtt tcacaagcaa tccagaggta cgctacgaag tctgtgacat    2100
tcctcagtgt tcagaagttg aatgcatgac ctgcaatggg gagagttatc gaggtctcat   2160
ggatcataca gaatcaggca agatttgtca gcgctgggat catcagacac cacaccggca   2220
caaattcttg cctgaaagat atcccgacaa gggctttgat gataattatt gccgcaatcc   2280
cgatggccag ccgaggccat ggtgctatac tcttgaccct cacacccgct gggagtactg   2340
tgcaattaaa acatgcgctg acaatactat gaatgacact gatgttcctt tggaaacaac   2400
tgaatgcatc caaggtcaag gagaaggcta caggggcact gtcaatacca tttggaatgg   2460
aattccatgt cagcgttggg attctcagta tcctcacgag catgacatga ctcctgaaaa   2520
tttcaagtgc aaggacctac gagaaaatta ctgccgaaat ccagatgggt ctgaatcacc   2580
ctggtgtttt accactgatc caaacatccg agttggctac tgctcccaaa ttccaaactg   2640
tgatatgtca catggacaag attgttatcg tgggaatggc aaaaattata tgggcaactt   2700
atcccaaaca agatctggac taacatgttc aatgtgggac aagaacatgg aagacttaca   2760
tcgtcatatc ttctgggaac cagatgcaag taagctgaat gagaattact gccgaaatcc   2820
agatgatgat gctcatggac cctggtgcta cacgggaaat ccactcattc cttgggatta   2880
ttgccctatt tctcgttgtg aaggtgatac cacacctaca atagtcaatt tagaccatcc   2940
cgtaatatct tgtgccaaaa cgaaacaatt gcgagttgta atgggattc caacacgaac    3000 aaacatagga tggatggtta gtttgagata cagaaataaa catatctgcg gaggatcatt   3060
gataaaggag agttgggttc ttactgcacg acagtgtttc ccttctcgag acttgaagaa   3120
ttatgaagct tggcttggaa ttcatgatgt ccacggaaga ggagatgaga atgcaaaca    3180 ggttctcaat gtttcccagc tggtatatgg ccctgaagga tcagatctgg ttttaatgaa   3240
gcttgccagg cctgctgtcc tggatgattt tgttagtacg attgatttac ctaattatgg   3300
```

```
atgcacaatt cctgaaaaga ccagttgcag tgtttatggc tggggctaca ctggattgat    3360
caactatgat ggcctattac gagtggcaca tctctatata tgggaaatg agaaatgcag     3420 ccagcatcat cgagggaagg tgactctgaa tgagtctgaa atatgtgctg ggctgaaaa     3480 gattggatca ggaccatgtg aggggatta tggtggccca cttgtttgtg agcaacataa     3540
aatgagaatg gttcttggtg tcattgttcc tggtcgtgga tgtgccattc caaatcgtcc    3600
tggtattttt gtccgagtag catattatgc aaaatggata cacaaaatta ttttaacata    3660
taaggtacca cagtcatag                                                 3679

<210> SEQ ID NO 10
<211> LENGTH: 2729
<212> TYPE: DNA
<213> ORGANISM: Artificial Sequence
<220> FEATURE:
<223> OTHER INFORMATION: Synthetic HGF-X8 gene

<400> SEQUENCE: 10
atgtgggtga ccaaactcct gccagccctg ctgctgcagc atgtcctcct gcatctcctc      60
ctgctcccca tcgccatccc ctatgcagag ggacaaagga aagaagaaa tacaattcat     120 gaattcaaaa aatcagcaaa gactacccta atcaaaatag atccagcact gaagataaaa    180
accaaaaaag tgaatactgc agaccaatgt gctaatagat gtactaggaa taaggacttc    240
ccattcactt gcaaggcttt tgttttgat aaagcaagaa acaatgcct ctggttcccc      300 ttcaatagca tgtcaagtgg agtgaaaaaa gaatttggcc atgaatttga cctctatgaa    360
aacaaagact acattagaaa ctgcatcatc ggtaaaggac gcagctacaa gggaacagta    420
tctatcacta gagtggcat caaatgtcag ccctggagtt ccatgatacc acacgaacac    480
aggtaagaac agtatgaaga aaagagatga agcctctgtc ttttttacat gttaacagtc    540
tcatattagt ccttcagaat aattctacaa tcctaaaata acttagccaa cttgctgaat    600
tgtattacgg caaggttat atgaattcat gactgatat tagcaaatga ttaattaata     660
tgttaataaa atgtagccaa acaatatct taccttaatg cctcaatttg tagatctcgg    720
tatttgtgga tccttatgtt tcagacaact tcgattcagt tctagaatgt ttgactcagc    780
aaattcacag gctcatcttt ctaacttgat ggtgaatatg gaaattcagc taaatggatg    840
ttaataaaat tcaacgtttt taaggacaga tgaaaatgac agaattttaa ggtaaaatat    900
atgaaggaat ataagataaa ggattttct accttcagca aaaacatacc cactaattag    960
taaaattaat aggcaaaaaa aagttgcatg ctcttatact gtaatgatta tcatttttaaa  1020 actagctttt tgccttcgag ctatcggggt aaagacctac aggaaaacta ctgtcgaaat    1080
cctcgagggg aagaagggg accctggtgt ttcacaagca atccagaggt acgctacgaa    1140
gtctgtgaca ttcctcagtg ttcagaagtt gaatgcatga cctgcaatgg ggagagttat    1200
cgaggtctca tggatcatac agaatcaggc aagatttgtc agcgctggga tcatcagaca    1260
ccacaccggc acaaattctt gcctgaaaga tatcccgaca agggctttga tgataattat    1320
tgccgcaatc ccgatggcca gccgaggcca tggtgctata ctcttgaccc tcacacccgc    1380
tgggagtact gtgcaattaa acatgcgct gacaatacta tgaatgacac tgatgttcct    1440
ttggaaacaa ctgaatgcat ccaaggtcaa ggagaaggct acaggggcac tgtcaatacc    1500
atttggaatg gaattccatg tcagcgttgg gattctcagt atcctcacga gcatgacatg    1560
actcctgaaa atttcaagtg caaggaccta cgagaaaatt actgccgaaa tccagatggt    1620
ctgaatcacc ctggtgtttt accactgatc caaacatccg agttggctac tgctcccaaa    1680
```

-continued

```
ttccaaactg tgatatgtca catggacaag attgttatcg tgggaatggc aaaaattata      1740
tgggcaactt atcccaaaca agatctggac taacatgttc aatgtgggac aagaacatgg      1800
aagacttaca tcgtcatatc ttctgggaac cagatgcaag taagctgaat gagaattact      1860
gccgaaatcc agatgatgat gctcatggac cctggtgcta cacgggaaat ccactcattc      1920
cttgggatta ttgccctatt tctcgttgtg aaggtgatac cacacctaca atagtcaatt      1980
tagaccatcc cgtaatatct tgtgccaaaa cgaaacaatt gcgagttgta aatgggattc      2040
caacacgaac aaacatagga tggatggtta gtttgagata cagaaataaa catatctgcg      2100
gaggatcatt gataaaggag agttgggttc ttactgcacg acagtgtttc ccttctcgag      2160
acttgaaaga ttatgaagct tggcttggaa ttcatgatgt ccacggaaga ggagatgaga      2220
aatgcaaaca ggttctcaat gtttcccagc tggtatatgg ccctgaagga tcagatctgg      2280
ttttaatgaa gcttgccagg cctgctgtcc tggatgattt tgttagtacg attgatttac      2340
ctaattatgg atgcacaatt cctgaaaaga ccagttgcag tgtttatggc tggggctaca      2400
ctggattgat caactatgat ggcctattac gagtggcaca tctctatata atgggaaatg      2460
agaaatgcag ccagcatcat cgagggaagg tgactctgaa tgagtctgaa atatgtgctg      2520
gggctgaaaa gattggatca ggaccatgtg agggggatta tggtggccca cttgtttgtg      2580
agcaacataa aatgagaatg gttcttggtg tcattgttcc tggtcgtgga tgtgccattc      2640
caaatcgtcc tggtattttt gtccgagtag catattatgc aaaatggata cacaaaatta      2700
ttttaacata taaggtacca cagtcatag                                        2729
```

<210> SEQ ID NO 11
<211> LENGTH: 285
<212> TYPE: PRT
<213> ORGANISM: Homo sapiens

<400> SEQUENCE: 11

```
Met Trp Val Thr Lys Leu Leu Pro Ala Leu Leu Leu Gln His Val Leu
1               5                   10                  15

Leu His Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Tyr Arg Gly Lys Asp Leu Gln Glu Asn Tyr Cys Arg Asn Pro Arg
                165                 170                 175

Gly Glu Glu Gly Gly Pro Trp Cys Phe Thr Ser Asn Pro Glu Val Arg
            180                 185                 190
```

```
Tyr Glu Val Cys Asp Ile Pro Gln Cys Ser Glu Val Glu Cys Met Thr
            195                 200                 205
Cys Asn Gly Glu Ser Tyr Arg Gly Leu Met Asp His Thr Glu Ser Gly
    210                 215                 220
Lys Ile Cys Gln Arg Trp Asp His Gln Thr Pro His Arg His Lys Phe
225                 230                 235                 240
Leu Pro Glu Arg Tyr Pro Asp Lys Gly Phe Asp Asp Asn Tyr Cys Arg
                245                 250                 255
Asn Pro Asp Gly Gln Pro Arg Pro Trp Cys Tyr Thr Leu Asp Pro His
            260                 265                 270
Thr Arg Trp Glu Tyr Cys Ala Ile Lys Thr Cys Glu Thr
            275                 280                 285

<210> SEQ ID NO 12
<211> LENGTH: 296
<212> TYPE: PRT
<213> ORGANISM: Homo sapiens

<400> SEQUENCE: 12

Met Trp Val Thr Lys Leu Leu Pro Ala Leu Leu Leu Gln His Val Leu
1               5                   10                  15
Leu His Leu Leu Leu Leu Pro Ile Ala Ile Pro Tyr Ala Glu Gly Gln
            20                  25                  30
Arg Lys Arg Arg Asn Thr Ile His Glu Phe Lys Lys Ser Ala Lys Thr
        35                  40                  45
Thr Leu Ile Lys Ile Asp Pro Ala Leu Lys Ile Lys Thr Lys Lys Val
    50                  55                  60
Asn Thr Ala Asp Gln Cys Ala Asn Arg Cys Thr Arg Asn Lys Gly Leu
65                  70                  75                  80
Pro Phe Thr Cys Lys Ala Phe Val Phe Asp Lys Ala Arg Lys Gln Cys
                85                  90                  95
Leu Trp Phe Pro Phe Asn Ser Met Ser Ser Gly Val Lys Lys Glu Phe
            100                 105                 110
Gly His Glu Phe Asp Leu Tyr Glu Asn Lys Asp Tyr Ile Arg Asn Cys
        115                 120                 125
Ile Ile Gly Lys Gly Arg Ser Tyr Lys Gly Thr Val Ser Ile Thr Lys
    130                 135                 140
Ser Gly Ile Lys Cys Gln Pro Trp Ser Ser Met Ile Pro His Glu His
145                 150                 155                 160
Ser Phe Leu Pro Ser Ser Tyr Arg Gly Lys Asp Leu Gln Glu Asn Tyr
                165                 170                 175
Cys Arg Asn Pro Arg Gly Glu Glu Gly Gly Pro Trp Cys Phe Thr Ser
            180                 185                 190
Asn Pro Glu Val Arg Tyr Glu Val Cys Asp Ile Pro Gln Cys Ser Glu
        195                 200                 205
Val Glu Cys Met Thr Cys Asn Gly Glu Ser Tyr Arg Gly Leu Met Asp
    210                 215                 220
His Thr Glu Ser Gly Lys Ile Cys Gln Arg Trp Asp His Gln Thr Pro
225                 230                 235                 240
His Arg His Lys Phe Leu Pro Glu Arg Tyr Pro Asp Lys Gly Phe Asp
                245                 250                 255
Asp Asn Tyr Cys Arg Asn Pro Asp Gly Gln Pro Arg Pro Trp Cys Tyr
            260                 265                 270
Thr Leu Asp Pro His Thr Arg Trp Glu Tyr Cys Ala Ile Lys Asn Met
        275                 280                 285
```

Arg Asp Ile Thr Trp Ala Leu Asn
    290             295

<210> SEQ ID NO 13
<211> LENGTH: 6190
<212> TYPE: DNA
<213> ORGANISM: Artificial Sequence
<220> FEATURE:
<223> OTHER INFORMATION: Synthetic Hepatocyte Growth Factor Hybrid
      (HGF)-X2

<400> SEQUENCE: 13

```
atgtgggtga ccaaactcct gccagccctg ctgctgcagc atgtcctcct gcatctcctc      60
ctgctcccca tcgccatccc ctatgcagag ggacaaagga aagaagaaa tacaattcat      120 gaattcaaaa aatcagcaaa gactacccta atcaaaatag atccagcact gaagataaaa      180
accaaaaaag tgaatactgc agaccaatgt gctaatagat gtactaggaa taaaggactt      240
ccattcactt gcaaggcttt tgttttttgat aaagcaagaa acaatgcct ctggttcccc      300 ttcaatagca tgtcaagtgg agtgaaaaaa gaatttggcc atgaatttga cctctatgaa      360
aacaaagact acattagaaa ctgcatcatt ggtaaaggca gcagctacaa gggaacagta      420
tctatcacta gagtggcat caaatgtcag ccctggagtt ccatgatacc acacgaacac      480
aggtaagaac agtatgaaga aaagagatga agcctctgtc ttttttacat gttaacagtc      540
tcatattagt ccttcagaat aattctacaa tcctaaaata acttagccaa cttgctgaat      600
tgtattacgg caaggtttat atgaattcat gactgatatt tagcaaatga ttaattaata      660
tgttaataaa atgtagccaa acaatatct taccttaatg cctcaatttg tagatctcgg      720
tatttgtgaa ataataacgt aaacttcgtt taaaaggatt cttcttcctg tctttgagaa      780
agtacggcac tgtgcagggg gagaggttga ttgtgaaaaa tcagaggtag atgagaatct      840
tactgagggc tgagggttct ttaaccttgg tggatctcaa cattggttgc acattaaaat      900
cacctgctgc aagcccttga cgaatcttac ttagaagatg acaacacaga acaattaaat      960
cagaatctct ggggagaata gggcaccagt attttttgag ctcccaccat gattccaaag     1020
tgcagccaaa tttgagaacc actgctaaaa gctcaagctt cagattgacc agcttttcca     1080
tctcacctat cgcctaaaga ccaaattgga taaatgtgtt cattacgaca gatgggtact     1140
atttaaagat gagtaaacac aatatactta ggctcgtcag actgagagtt ttaatcatca     1200
ctgaggaaaa acatagatat ctaatactga ctggagtatt agtcaaggct tatttcacac     1260
acaattttat cagaaaccaa agtagtttaa aacagctctc cccttattag taatgcattg     1320
gagggtttac tttaccatgt accttgctga gcactgtacc ttgttaatct catttacttg     1380
taatgagaac cacacagcgg gtagtttat tggttctatt ttacctacat gacaaaactg     1440
aagcataaaa acacttagta agttttcagt gtcatgcaca actaggaagt gacatggcca     1500
gaatataagc ccagtcacca tcactctata acctgcgctt taacaacttt cagggcatga     1560
cacatttggc cggtcagtag aacccatgct gtgatttgtt tttgcagtgg tggtgatgac     1620
tgccttgttg aatccacttt ttattctatt ccatttgggg gacacaattc tgcaagatga     1680
ttcttcatta ggaaacagag atgagttatt gaccaacaca gaaagaaaaa gagtttgttg     1740
ctccacactg ggattaaacc tatgatcttg gcctaattaa cactagctag taagtgtcca     1800
agctgatcat ctctacaaca tttcaataac agaaaacaac aattttcaaa attagttact     1860
tacaattatg tagaaatgcc tctaaaacac agtattttcc ttatattaca aaaacaaaaa     1920
ttataattgg ttttgtcctc ttttgagagt ttgcatggtg ttactccctg catagtgaag     1980
```

```
aaaacatttt atttaagtag atggatctaa gtttttcatg aacaaaggaa tgacatttga    2040
aatcaatcct accctagtcc aggagaatgc attagattaa cctagtagag gtcttatttc    2100
accctgagtt ttctatgatc gtgattctct gctggaggag taattgtgaa atagatctct    2160
ctgggaactg gcttcctagt ccaatcagct cttttaccaa tgaacacttc cttgtgatat    2220
agatgtttat ggccgagagg atcccttcct ttctacctgt atttgtccta ataaattgtt    2280
gacttattaa ttcactactt cctcacagct ttttttggc tttacaaatc cactggaaag    2340
gtatatgggt gtatcacttt gtgtatttcg gtgtgcatgt gtagagggga caaaaatcct    2400
ctctcaaact ataaatattg agtatttgtg tattgaacat ttgctataac tactaggttt    2460
cttaaataat cttaatatat aaatgatat agaaaaaggg aaattatagt tcgtattatt    2520
catctaagtg aagagattaa aacccaggga gtaaataaat tgtctaagga ctaaggttgt    2580
atactattta ggtgatagat atggggcaac cgtatgggtt ttatgattaa caaataaact    2640
tctcaccact ctaccatatc aacttttcca taaaagagag ctatagtatt ctttgcttaa    2700
ataaatttga ttagtgcatg acttcttgaa aacatataaa gcaaaagtca catttgattc    2760
tatcagaaaa gtgagtaagc catggcccaa acaaagatg cattaaaata ttctggaatg     2820
atggagctaa aagtaagaaa aatgactttt taaaaaagtt tactgttagg aattgtgaaa    2880
ttatgctgaa ttttagttgc attataattt ttgtcagtca tacggtctga caacctgtct    2940
tatttctatt tccccatatg aggaatgcta gttaagtatg gatattaact attactactt    3000
agatgcattg aagttgcata atatggataa tacttcactg gttccctgaa aatgtttagt    3060
tagtaataag tctcttacac tatttgtttt gtccaataat ttatattttc tgaagactta    3120
actctagaat acactcatgt caaaatgaaa gaatttcatt gcaaaatatt gcttggtaca    3180
tgacgcatac ctgtatttgt tttgtgtcac aacatgaaaa atgatggttt attagaagtt    3240
tcattgggta ggaaacacat ttgaatggta tttactaaga tactaaaatc cttggacttc    3300
actctaattt tagtgccatt tagaactcaa ggtctcagta aaagtagaaa taaagcctgt    3360
taacaaaaca caaactgaat attaaaaatg taactggatt ttcaaagaaa tgtttactgg    3420
tattacctgt agatgtatat tcttttattat gatcttttgt gtaaagtctg gcagacaaat    3480
gcaatatcta attgttgagt ccaatatcac aagcagtaca aaagtataaa aaagacttgg    3540
ccttttctaa tgtgttaaaa tactttatgc tggtaataac actaagagta gggcactaga    3600 aatttttaagt gaagataatg tgttgcagtt actgcactca atggcttact attataaacc    3660
aaaactggga tcactaagct ccagtcagtc aaaatgatca aaattattga agagaataag    3720
caattctgtt cttttattagg acacagtaga tacagactac aaagtggagt gtgcttaata    3780
agaggtagca tttgttaagt gtcaattact ctattatccc ttggagcttc tcaaaataac    3840
catataaggt gtaagatgtt aaaggttatg gttacactca gtgcacaggt aagctaatag    3900
gctgagagaa gctaaattac ttactggggt ctcacagtaa gaaagtgagc tgaagtttca    3960
gcccagattt aactggattc tgggctcttt attcatgtta cttcatgaat ctgtttctca    4020
attgtgcaga aaaagggggg ctatttataa gaaaagcaat aaacaaacaa gtaatgatct    4080
caaataagta atgcaagaaa tagtgagatt tcaaaatcag tggcagcgat ttctcagttc    4140
tgtcctaagt ggccttgctc aatcacctgc tatcttttag tggagctttg aaattatgtt    4200
tcagacaact tcgattcagt tctagaatgt ttgactcagc aaattcacag gctcatcttt    4260
ctaacttgat ggtgaatatg gaattcagc taaatggatg ttaataaaat tcaaacgttt     4320
taaggacaga tggaaatgac agaattttaa ggtaaaatat atgaaggaat ataagataaa    4380
```

-continued

```
ggattttct accttcagca aaaacatacc cactaattag taaaattaat aggcgaaaaa    4440
aagttgcatg ctcttatact gtaatgatta tcattttaaa actagctttt tgccttcgag    4500 ctatcgggt aaagacctac aggaaaacta ctgtcgaaat cctcgagggg aagaaggggg     4560
accctggtgt ttcacaagca atccagaggt acgctacgaa gtctgtgaca ttcctcagtg    4620
ttcagaagtt gaatgcatga cctgcaatgg ggagagttat cgaggtctca tggatcatac    4680
agaatcaggc aagatttgtc agcgctggga tcatcagaca ccacaccggc acaaattctt    4740
gcctgaaaga tatcccgaca agggctttga tgataattat tgccgcaatc ccgatggcca    4800
gccgaggcca tggtgctata ctcttgaccc tcacacccgc tgggagtact gtgcaattaa    4860
aacatgcgct gacaatacta tgaatgacac tgatgttcct ttggaaacaa ctgaatgcat    4920
ccaaggtcaa ggagaaggct acaggggcac tgtcaatacc atttggaatg gaattccatg    4980
tcagcgttgg gattctcagt atcctcacga gcatgacatg actcctgaaa atttcaagtg    5040
caaggaccta cgagaaaatt actgccgaaa tccagatggg tctgaatcac cctggtgttt    5100
taccactgat ccaaacatcc gagttggcta ctgctcccaa attccaaact gtgatatgtc    5160
acatggacaa gattgttatc gtgggaatgg caaaaattat atgggcaact tatcccaaac    5220
aagatctgga ctaacatgtt caatgtggga caagaacatg gaagacttac atcgtcatat    5280
cttctgggaa ccagatgcaa gtaagctgaa tgagaattac tgccgaaatc cagatgatga    5340
tgctcatgga ccctggtgct acacgggaaa tccactcatt ccttgggatt attgccctat    5400
ttctcgttgt gaaggtgata ccacacctac aatagtcaat ttagaccatc ccgtaatatc    5460
ttgtgccaaa acgaaacaat gcgagttgt aaatgggatt ccaacacgaa caaacatagg     5520
atggatggtt agtttgagat acagaaataa acatatctgc ggaggatcat tgataaagga    5580
gagttgggtt cttactgcac gacagtgttt cccttctcga gacttgaaag attatgaagc    5640
ttggcttgga attcatgatg tccacggaag aggagatgag aaatgcaaac aggttctcaa    5700
tgtttcccag ctggtatatg gccctgaagg atcagatctg gttttaatga agcttgccag    5760
gcctgctgtc ctggatgatt ttgttagtac gattgattta cctaattatg gatgcacaat    5820
tcctgaaaag accagttgca gtgtttatgg ctggggctac actggattga tcaactatga    5880
tggcctatta cgagtggcac atctctatat aatgggaaat gagaaatgca gccagcatca    5940
tcgagggaag gtgactctga atgagtctga aatatgtgct ggggctgaaa agattggatc    6000
aggaccatgt gaggggggatt atggtggccc acttgtttgt gagcaacata aaatgagaat    6060
ggttcttggt gtcattgttc ctggtcgtgg atgtgccatt ccaaatcgtc ctggtatttt    6120
tgtccgagta gcatattatg caaaatggat acacaaaatt atttaacat ataaggtacc      6180 acagtcatag                                                           6190
```

<210> SEQ ID NO 14
<211> LENGTH: 5190
<212> TYPE: DNA
<213> ORGANISM: Artificial Sequence
<220> FEATURE:
<223> OTHER INFORMATION: Synthetic Hepatocyte Growth Factor Hybrid
      (HGF)-X3

<400> SEQUENCE: 14

```
atgtgggtga ccaaactcct gccagccctg ctgctgcagc atgtcctcct gcatctcctc       60
ctgctcccca tcgccatccc ctatgcagag ggacaaagga aagaagaaa tacaattcat      120 gaattcaaaa aatcagcaaa gactacccta atcaaaatag atccagcact gaagataaaa      180
```

```
accaaaaaag tgaatactgc agaccaatgt gctaatagat gtactaggaa taaaggactt    240
ccattcactt gcaaggcttt tgtttttgat aaagcaagaa acaatgcct  ctggttcccc    300 ttcaatagca tgtcaagtgg agtgaaaaaa gaatttggcc atgaatttga cctctatgaa    360
aacaaagact acattagaaa ctgcatcatt ggtaaaggac gcagctacaa gggaacagta    420
tctatcacta agagtggcat caaatgtcag ccctggagtt ccatgatacc acacgaacac    480
aggtaagaac agtatgaaga aaagagatga agcctctgtc ttttttacat gttaacagtc    540
tcatattagt ccttcagaat aattctacaa tcctaaaata acttagccaa cttgctgaat    600
tgtattacgg caaggtttat atgaattcat gactgatatt tagcaaatga ttaattaata    660
tgttaataaa atgtagccaa acaatatct  taccttaatg cctcaatttg tagatctcgg    720
tatttgtgaa ataataacgt aaacttcgtt taaaaggatt cttcttcctg tctttgagaa    780
agtacggcac tgtgcagggg gagaggttga ttgtgaaaaa tcagaggtag atgagaatct    840
tactgagggc tgagggttct ttaaccttgg tggatctcaa cattggttgc acattaaaat    900
cacctgctgc aagcccttga cgaatcttac ttagaagatg acaacacaga acaattaaat    960
cagaatctct ggggagaata gggcaccagt atttttttgag ctcccaccat gattccaaag   1020
tgcagccaaa tttgagaacc actgctaaaa gctcaagctt cagattgacc agcttttcca   1080
tctcacctat cgcctaaaga ccaaattgga taaatgtgtt cattacgaca gatgggtact   1140
atttaaagat gagtaaacac aatatactta ggctcgtcag actgagagtt ttaatcatca   1200
ctgaggaaaa acatagatat ctaatactga ctggagtatt agtcaaggct tatttcacac   1260
acaattttat cagaaaccaa agtagtttaa aacagctctc cccttattag taatgcattg   1320
gagggtttac tttaccatgt accttgctga gcactgtacc ttgttaatct catttacttg   1380
taatgagaac cacacagcgg gtagttttat tggttctatt ttacctacat gacaaaactg   1440
aagcataaaa acacttagta agttttcagt gtcatgcaca actaggaagt gacatggcca   1500
gaatataagc ccagtcacca tcactctata acctgcgctt ttaacaactt cagggcatga   1560
cacatttggc cggtcagtag aacccatgct gtgatttgtt tttgcagtgg tggtgatgac   1620
tgccttgttg aatccacttt ttattctatt ccatttgggg gacacaattc tgcaagatga   1680
ttcttcatta ggaaacagag atgagttatt gaccaacaca gaaagaaaaa gagtttgttg   1740
ctccacactg ggattaaacc tatgatcttg gcctaattaa cactagctag taagtgtcca   1800
agctgatcat ctctacaaca tttcaataac agaaacaac  aattttcaaa attagttact   1860
tacaattatg tagaaatgcc tctaaaacac agtattttcc ttatattaca aaacaaaaa    1920 ttataattgg ttttgtcctc ttttgagagt ttgcatggtg ttactccctg catagtgaag   1980
aaaacatttt atttaagtag atggatctaa gttttcatg  aacaaaggaa tgacatttga   2040
aatcaatcct accctagtcc aggagaatgc attagattaa cctagtagag gtcttatttc   2100
accctgagtt ttctatgatc gtgattctct gctggaggag taattgtgaa atagatctct   2160
ctgggaactg gcttcctagt ccaatcagct cttttaccaa tgaacacttc cttgtgatat   2220
agatgtttat ggccgagagg atcctgggta ggaaacacat ttgaatggta tttactaaga   2280
tactaaaatc cttggacttc actctaattt tagtgccatt tagaactcaa ggtctcagta   2340
aaagtagaaa taaagcctgt taacaaaaca caaactgaat attaaaaatg taactggatt   2400
ttcaaagaaa tgtttactgg tattacctgt agatgtatat tctttattat gatcttttgt   2460
gtaaagtctg gcagacaaat gcaatatcta attgttgagt ccaatatcac aagcagtaca   2520
aaagtataaa aaagacttgg ccttttctaa tgtgttaaaa tactttatgc tggtaataac   2580
```

```
actaagagta gggcactaga aattttaagt gaagataatg tgttgcagtt actgcactca   2640
atggcttact attataaacc aaaactggga tcactaagct ccagtcagtc aaaatgatca   2700
aaattattga agagaataag caattctgtt ctttattagg acacagtaga tacagactac   2760
aaagtggagt gtgcttaata agaggtagca tttgttaagt gtcaattact ctattatccc   2820
ttggagcttc tcaaaataac catataaggt gtaagatgtt aaaggttatg gttacactca   2880
gtgcacaggt aagctaatag gctgagagaa gctaaattac ttactggggt ctcacagtaa   2940
gaaagtgagc tgaagtttca gcccagattt aactggattc tgggctcttt attcatgtta   3000
cttcatgaat ctgtttctca attgtgcaga aaaaggggg ctatttataa gaaaagcaat   3060
aaacaaacaa gtaatgatct caaataagta atgcaagaaa tagtgagatt caaaatcag   3120 tggcagcgat ttctcagttc tgtcctaagt ggccttgctc aatcacctgc tatcttttag   3180
tggagctttg aaattatgtt tcagacaact tcgattcagt tctagaatgt ttgactcagc   3240
aaattcacag gctcatcttt ctaacttgat ggtgaatatg gaaattcagc taaatggatg   3300
ttaataaaat tcaaacgttt taaggacaga tggaaatgac agaattttaa ggtaaaatat   3360
atgaaggaat ataagataaa ggattttct accttcagca aaaacatacc cactaattag   3420
taaaattaat aggcgaaaaa aagttgcatg ctcttatact gtaatgatta tcattttaaa   3480
actagctttt tgccttcgag ctatcggggt aaagacctac aggaaaacta ctgtcgaaat   3540
cctcgagggg aagaagggg accctggtgt ttcacaagca atccagaggt acgctacgaa   3600
gtctgtgaca ttcctcagtg ttcagaagtt gaatgcatga cctgcaatgg ggagagttat   3660
cgaggtctca tggatcatac agaatcaggc aagatttgtc agcgctggga tcatcagaca   3720
ccacaccggc acaaattctt gcctgaaaga tatcccgaca agggctttga tgataattat   3780
tgccgcaatc ccgatggcca gccgaggcca tggtgctata ctcttgaccc tcacacccgc   3840
tgggagtact gtgcaattaa acatgcgct gacaatacta tgaatgacac tgatgttcct   3900
ttggaaacaa ctgaatgcat ccaaggtcaa ggagaaggct acaggggcac tgtcaatacc   3960
atttggaatg gaattccatg tcagcgttgg gattctcagt atcctcacga gcatgacatg   4020
actcctgaaa atttcaagtg caaggaccta cgagaaaatt actgccgaaa tccagatggg   4080
tctgaatcac cctggtgttt taccactgat ccaaacatcc gagttggcta ctgctcccaa   4140
attccaaact gtgatatgtc acatggacaa gattgttatc gtgggaatgg caaaaattat   4200
atgggcaact tatcccaaac aagatctgga ctaacatgtt caatgtggga caagaacatg   4260
gaagacttac atcgtcatat cttctgggaa ccagatgcaa gtaagctgaa tgagaattac   4320
tgccgaaatc cagatgatga tgctcatgga ccctggtgct acacgggaaa tccactcatt   4380
ccttgggatt attgccctat ttctcgttgt gaaggtgata ccacacctac aatagtcaat   4440
ttagaccatc ccgtaatatc ttgtgccaaa acgaaacaat gcgagttgt aaatgggatt   4500 ccaacacgaa caaacatagg atggatggtt agtttgagat acagaaataa acatatctgc   4560
ggaggatcat tgataaagga gagttgggtt cttactgcac gacagtgttt cccttctcga   4620
gacttgaaag attatgaagc ttggcttgga attcatgatg tccacggaag aggagatgag   4680
aaatgcaaac aggttctcaa tgtttcccag ctggtatatg gccctgaagg atcagatctg   4740
gttttaatga agcttgccag gcctgctgtc ctggatgatt ttgttagtac gattgattta   4800
cctaattatg gatgcacaat tcctgaaaag accagttgca gtgtttatgg ctgggggctac   4860 actgattga tcaactatga tggcctatta cgagtggcac atctctatat aatgggaaat   4920
gagaaatgca gccagcatca tcgagggaag gtgactctga atgagtctga aatatgtgct   4980
```

```
ggggctgaaa agattggatc aggaccatgt gaggggatt atggtggccc acttgtttgt    5040
gagcaacata aaatgagaat ggttcttggt gtcattgttc ctggtcgtgg atgtgccatt    5100
ccaaatcgtc ctggtatttt tgtccgagta gcatattatg caaaatggat acacaaaatt    5160
attttaacat ataaggtacc acagtcatag                                    5190
```

LYOPHILIZED DNA FORMULATIONS FOR ENHANCED EXPRESSION OF PLASMID DNA

This application is a divisional of U.S. application Ser. No. 12/421,425, filed Apr. 9, 2009, which claims priority to U.S. Provisional Appl. No. 61/043,605, filed on Apr. 9, 2008, the entire contents of each are hereby incorporated by reference in their entirety.

REFERENCE TO A SEQUENCE LISTING SUBMITTED ELECTRONICALLY VIA EFS-WEB

The content of the electronically submitted sequence listing (Name: Sequence_Listing_Ascii.txt, Size: 68,654 bytes; and Date of Creation: Apr. 8, 2009) filed herewith with the application is incorporated by reference in its entirety.

BACKGROUND OF THE INVENTION

Lyophilization is often a preferred formulation for therapeutic materials because the long-term stability of many materials increases in the lyophilized state. However, for plasmid DNA, lyophilized formulations are not the formulations of choice. In most clinical trials using naked (non-complexed plasmid) DNA as a delivery vector, the preferred formulation has been a liquid formulation.

While lyophilized plasmid DNA may be a preferred form of storage, lyophilized formulations for plasmid DNA have been considered to cause a reduction in gene expression efficiency. Lyophilization causes the removal of the hydration sphere around a molecule. For DNA, it appears that there are approximately 20 water molecules per nucleotide pair bound most tightly to DNA that do not form an ice-like structure upon low-temperature cooling. Upon DNA dehydration over hygroscopic salts at 0% relative humidity, only five or six water molecules remain. Thus, lyophilization may increase the stability of DNA under long-term storage, but may also cause some damage upon the initial lyophilization process, potentially through changes in the DNA secondary structure or the concentration of reactive elements such as contaminating metals. Therefore, a potential mechanism for loss of gene expression efficiency of lyophilized plasmid DNA may be through a gross structural change to the plasmid.

In Poxon et al, *Pharmaceutical Development and Technology* 5:115-122 (2000), the authors demonstrated that lyophilization of a plasmid DNA (pRL-CMV) resulted in a statistically significant loss of transfection efficiency. A biofunctionality assay, measuring transfection activity, demonstrated a loss of more than 75% of plasmid DNA activity after lyophilization as compared to control plasmid that remained in solution. While Poxon et al used carbohydrates to ameliorate the in vitro decreased transfection activity of a non-therapeutic plasmid, pRL-CMV expressing Renilla luciferase, stored in EDTA buffer, Poxon et al did not address the use of lyophilized naked DNA formulations in vivo for disease treatment or prevention.

Therefore, there is a need in the art for a stable lyophilized formulation that will not affect gene expression efficiency. The present invention provides for a lyophilized formulation for plasmid DNA that not only preserves the biological activity of the expressed gene but, in certain instances, is able to enhance biological activity.

BRIEF SUMMARY OF THE INVENTION

The present invention is directed to a lyophilized DNA formulation. In one aspect of the invention, a DNA formulation, prior to lyophilization, comprises a plasmid DNA, salt and a carbohydrate; and where the plasmid DNA comprises an HGF gene, or variant thereof. In another aspect of the invention, the DNA formulation is lyophilized. In another aspect of the invention, the lyophilized DNA formulation is reconstituted.

In one embodiment, the carbohydrate of the DNA formulation of the present invention is a mono-, oligo-, or polysaccharide such as sucrose, glucose, lactose, trehalose, arabinose, pentose, ribose, xylose, galactose, hexose, idose, mannose, talose, heptose, fructose, gluconic acid, sorbitol, mannitol, methyl α-glucopyranoside, maltose, isoascorbic acid, ascorbic acid, lactone, sorbose, glucaric acid, erythrose, threose, allose, altrose, gulose, erythrulose, ribulose, xylulose, psicose, tagatose, glucuronic acid, galacturonic acid, mannuronic acid, glucosamine, galactosamine, neuraminic acid, arabinans, fructans, fucans, galactans, galacturonans, glucans, mannans, xylans, levan, fucoidan, carrageenan, galactocarolose, pectins, pectic acids, amylose, pullulan, glycogen, amylopectin, cellulose, dextran, cyclodextrin, pustulan, chitin, agarose, keratin, chondroitin, dermatan, hyaluronic acid, alginic acid, xantham gum, or starch.

In certain embodiments of the invention, the carbohydrate is sucrose or mannitol.

In another embodiment, the carbohydrate of the DNA formulation of the present invention is in an amount selected from the group consisting of between about 0.05% to about 30%, between about 0.1% to about 15%, between about 0.2% to about 10%, between about 0.5% and 5%, between about 0.75% and 3%, between about 0.8% and 2%, and between about 0.8% and 1.5%. In particular embodiments, the carbohydrate is sucrose or mannitol. In certain other embodiments, the carbohydrate of the DNA formulation is in an amount of about 1.1%.

In another embodiment, the salt of the DNA formulation is selected from the group consisting of NaCl or KCl. In further embodiments, the salt of the DNA formulation is in an amount selected from the group consisting of between about 0.01% and 10%, between about 0.1% and 5%, between about 0.1% and 4%, between about 0.5% and 2%, between about 0.8% and 1.5%, between about 0.8% and 1.2% w/v. In certain embodiments, the salt of the DNA formulation is in an amount of about 0.9% w/v.

In another embodiment, the plasmid DNA of the invention comprises an HGF gene, or variant thereof. In certain embodiments, the HGF gene is a mammalian HGF gene or variant thereof. In further embodiments, the HGF gene is a human HGF gene or variant thereof. In certain aspects of the invention, the HGF gene is a hybrid HGF gene, e.g., a hybrid HGF gene comprising HGF cDNA and an inherent or foreign intron or fragment thereof, e.g., an inherent intron 4 or fragment thereof of the human HGF gene. In particular embodiments, the hybrid HGF gene comprises HGF-X2 (SEQ ID NO: 13), HGF-X3 (SEQ ID NO: 14), HGF-X6 (SEQ ID NO: 8), HGF-X7 (SEQ ID NO: 9) or HGF-X8 (SEQ ID NO: 10). In further embodiments, the plasmid DNA comprising a hybrid HGF gene is selected from the group consisting of: pCK-HGF-X2, pCK-HGF-X3, pCK-HGF-X6, pCK-HGF-X7, pCK-HGF-X8, pCP-HGF-X2, pCP-HGF-X3, pCP-HGF-X6, pCP-HGF-X7 and pCP-HGF-X8, where the HGF-X2, HGF-X3, HGF-X6, HGF-X7 and HGF-X8 correspond to SEQ ID NOs: 13-14 and 8-10, respectively.

The lyophilized DNA formulations maintain or enhance the expression of the plasmid DNA. In certain aspects, the lyophilized DNA formulation provides enhanced biological activity of the expressed protein. In certain other aspects of the invention, the enhanced expression of the plasmid DNA or the enhanced biological activity of the expressed protein is due to the presence of the carbohydrate in the formulation. In certain embodiments, this carbohydrate is sucrose or mannitol.

The invention also provides for a reconstituted lyophilized plasmid DNA formulation. In certain embodiments, the lyophilized DNA is reconstituted in a pharmaceutically acceptable solution. In further embodiments, the pharmaceutically acceptable solution is selected from the group consisting of water, PBS, TE, Tris buffer and normal saline.

In another embodiment, the plasmid DNA of the reconstituted lyophilized formulation is at a final concentration of about 1 ng/mL, about 5 ng/mL, about 10 ng/mL, about 50 ng/mL, about 100 ng/mL, about 250 ng/mL, about 500 ng/mL, about 1 µg/mL, about 5 µg/mL, about 10 µg/mL, about 50 µg/mL, about 100 µg/mL, about 200 µg/mL, about 300 µg/mL, about 400 µg/mL, about 500 µg/mL, about 600 µg/mL, about 700 µg/mL, about 800 µg/mL, about 900 µg/mL, about about 1 mg/mL, about 2 mg/mL, about 2.5 mg/mL, about 3 mg/mL, about 3.5 mg/mL, about 4 mg/mL, about 4.5 mg/mL, about 5 mg/mL, about 5.5 mg/mL, about 6 mg/mL, about 7 mg/mL, about 8 mg/mL, about 9 mg/mL, about 10 mg/mL, about 20 mg/mL, or about 30 mg/mL. In another embodiment, the final concentration of the plasmid DNA of the reconstituted lyophilized formulation is from about 1 ng/mL to about 30 mg/mL. In certain aspects, the final concentration of the plasmid DNA of the reconstituted lyophilized formulation is from about 100 µg/mL to about 2.5 mg/mL. In further aspects, the final concentration of the plasmid DNA of the reconstituted lyophilized formulation is from about 500 µg/mL to about 1 mg/mL.

The present invention is also directed to a method of treating or preventing ischemic or liver disease in a subject, comprising administering a composition reconstituted from a lyophilized hepatocyte growth factor (HGF) DNA formulation, where the DNA formulation comprises a plasmid DNA, salt and a carbohydrate; and where the plasmid DNA comprises an HGF gene, or variant thereof. In certain aspects, the composition reconstituted from a lyophilized HGF DNA formulation is administered by direct injection.

The present invention is further directed to a method of making a lyophilized HGF DNA formulation comprising: (a) preparing a DNA formulation comprising a plasmid DNA, a salt and a carbohydrate, where the plasmid DNA comprises an HGF gene, or variant thereof; and (b) lyophilizing the DNA formulation.

The steps for lyophilization may include subjecting a DNA formulation of the invention to the process of being frozen at subzero temperatures (e.g., −10° C. to −50° C.), and then subjected to one or more drying cycles which comprises gradually heating the DNA formulation to a temperature of about 20° C. to less than or equal to about 30° C., wherein the lyophilization occurs over a period of about 50 to about 100 hours. In a further aspect of the invention, the method for lyophilization comprises: (a) forming an aqueous DNA formulation comprising a plasmid DNA, a salt and a carbohydrate, where the plasmid DNA comprises an HGF gene, or variant thereof; (b) cooling the DNA formulation solution to a temperature of about −10° C. to about −50° C., until frozen; (c) drying the DNA formulation by heating to a temperature of about 20° C. to about 30° C.; and (d) recovering a lyophilized DNA formulation composition having a water content of from about 0.1 weight percent to about 5 weight percent based on the total weight of the recovered DNA formulation.

In certain embodiments, the DNA formulation is lyophilized under conditions comprising (a) about 30 hours to about 50 hours at a temperature greater than or equal to about −50° C. and less than about 0° C., and (b) about 20 hours to about 50 hours at a temperature greater than or equal to about 0° C. to less than or equal to about 30° C., progressively, wherein the lowest (a) temperature is about −50° C. to about −30° C. and the highest (b) temperature is between about 20° C. to about 30° C. In one aspect, the DNA formulation is lyophilized under conditions of −50° C. for 4 hours, −40° C. for 12 hours, −30° C. for 6 hours, −20° C. for 6 hours, −10° C. for 6 hours, 0° C. for 6 hours, 10° C. for 6 hours and 30° C. for 24 hours, progressively. In another aspect, the DNA formulation is lyophilized under conditions of 5° C. for 1 minute, −50° C. for 2 hours, −40° C. for 6 hours, −35° C. for 3 hours, −30° C. for 6 hours, −25° C. for 3 hours, −20° C. for 3 hours, −15° C. for 3 hours, −10° C. for 6 hours, −5° C. for 3 hours, 0° C. for 6 hours, and 30° C. for 17 hours, progressively. In another aspect, the DNA formulation is lyophilized under conditions of 5° C. for 1 minute, −10° C. for 1 minute, −20° C. for 1 minute, −30° C. for 1 minute, −50° C. for 1 minute, −50° C. for 2 hours, −45° C. for 6 hours, −40° C. for 3 hours, −35° C. for 6 hours, −30° C. for 3 hours, −25° C. for 6 hours, −20° C. for 3 hours, −15° C. for 6 hours, −10° C. for 3 hours, −5° C. for 6 hours, 0° C. for 12 hours, 10° C. for 3 hours, 20° C. for 6 hours, and 30° C. for 29 hours, progressively.

The invention is further directed to a lyophilized nucleic acid formulation or a reconstituted lyophilized nucleic acid formulation, as set forth above, where the nucleic acid is an RNA that encodes for HGF, or variant thereof.

DETAILED DESCRIPTION OF THE INVENTION

Definitions

Figure 1:
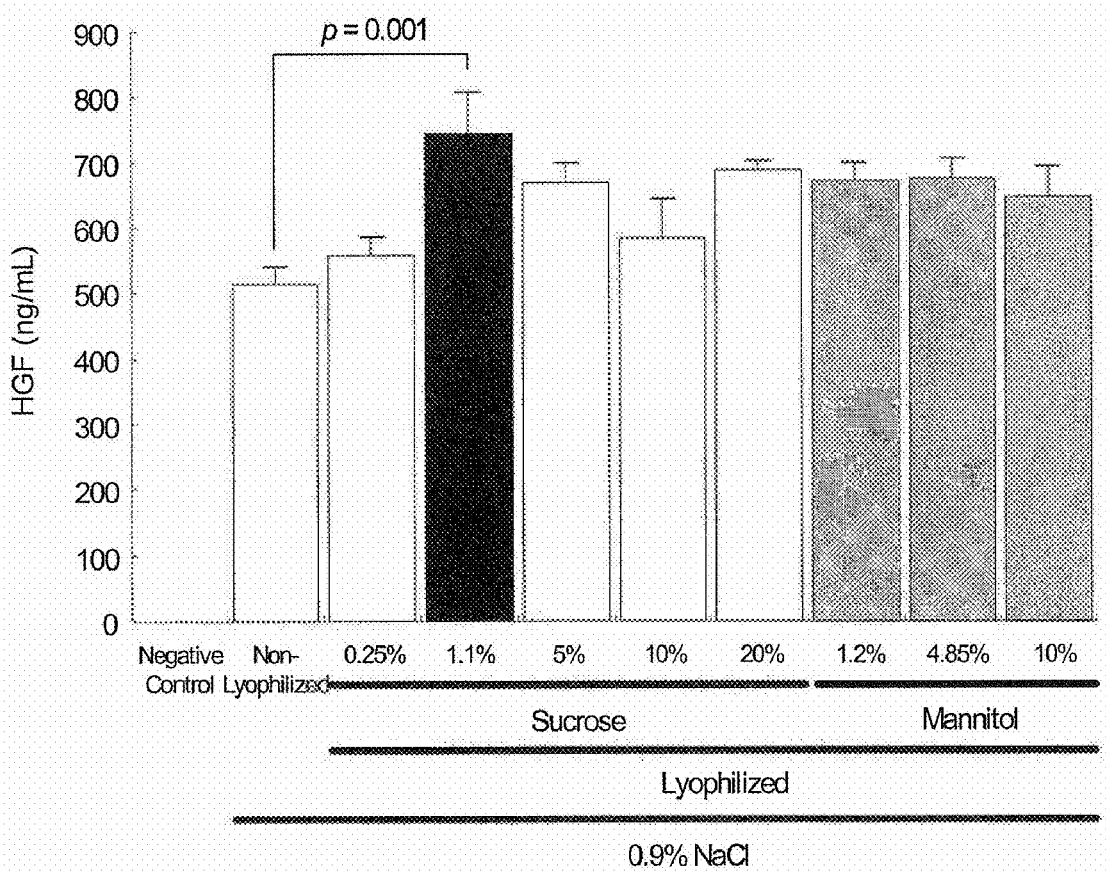
FIG. 1 depicts a bar graph comparing in vitro HGF expression among various formulations. HGF expression levels were measured using ELISA in culture supernatants isolated from 293T cells transfected with a lyophilized plasmid DNA pCK-HGF-X7 formulated in 0.9% NaCl at a final DNA concentration of 0.5 mg/mL, with sucrose at 0.25% (lane 3), 1.1% (lane 4), 5% (lane 5), 10% (lane 6) or 20% (lane 7) or with mannitol at 1.2% (lane 8), 4.85% (lane 9) or 10% (lane 10). Control reactions with a negative control (lane 1) and non-lyophilized DNA (lane 2) were used as comparison.

The term "DNA" or "nucleic acid" or "nucleic acid fragment" refers to any one or more nucleic acid segments, e.g., DNA or RNA fragments, present in a polynucleotide or construct. A nucleic acid or fragment thereof may be provided in linear (e.g., mRNA) or circular (e.g., plasmid) form as well as double-stranded or single-stranded forms. By "isolated" nucleic acid or polynucleotide is intended a nucleic acid molecule, DNA or RNA, which has been removed from its native environment. For example, a recombinant polynucleotide contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of the polynucleotides of the present invention. Isolated polynucleotides or nucleic acids according to the present invention further include such molecules produced synthetically.

As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, and the like, are not part of a coding region. Two or more nucleic acids or nucleic acid fragments of the present invention can be present in a single polynucleotide construct, e.g., on a single plasmid, or in separate polynucleotide constructs, e.g., on separate (different) plasmids. Furthermore, any nucleic acid or nucleic acid fragment may encode a single HGF polypeptide or fragment, derivative, or variant thereof, e.g., or may encode more than one polypeptide, e.g., a nucleic acid may encode two or more polypeptides. In addition, a nucleic acid may include a regulatory element such as a promoter, ribosome binding site, or a transcription terminator, or may encode heterologous coding regions fused to the HGF coding region, e.g., specialized elements or motifs, such as a secretory signal peptide or a heterologous functional domain.

In the case of DNA, a polynucleotide comprising a nucleic acid which encodes a polypeptide normally also comprises a promoter and/or other transcription or translation control elements operably associated with the polypeptide-encoding nucleic acid fragment. An operable association is when a nucleic acid fragment encoding a gene product, e.g., a polypeptide, is associated with one or more regulatory sequences in such a way as to place expression of the gene product under the influence or control of the regulatory sequence(s).

A DNA polynucleotide of the present invention may be a circular or linearized plasmid or vector, or other linear DNA which may also be non-infectious and nonintegrating (i.e., does not integrate into the genome of vertebrate cells). A linearized plasmid is a plasmid that was previously circular but has been linearized, for example, by digestion with a restriction endonuclease. As used herein, the terms plasmid and vector can be used interchangeably.

The term "lyophilized DNA" refers to any DNA that is prepared in dry form by rapid freezing and dehydration, in the frozen state under high vacuum. "Lyophilizing" or "lyophilization" refers to a process of freezing and drying a solution. Lyophilized DNA is often made ready for use by addition of sterile distilled water.

A "vector" refers to any vehicle for the cloning of and/or transfer of a nucleic acid into a host cell. A vector may be a replicon to which another DNA segment may be attached so as to bring about the replication of the attached segment. A "replicon" refers to any genetic element (e.g., plasmid, phage, cosmid, chromosome, virus) that functions as an autonomous unit of DNA replication in vivo, i.e., capable of replication under its own control. The term "vector" includes vehicles for introducing the nucleic acid into a cell in vitro, ex vivo or in vivo. A large number of vectors known in the art may be used to manipulate nucleic acids, incorporate response elements and promoters into genes, etc. Possible vectors include, for example, plasmids such as pBR322 or pUC plasmid derivatives, or the Bluescript vector. For example, the insertion of the DNA fragments corresponding to response elements and promoters into a suitable vector can be accomplished by ligating the appropriate DNA fragments into a chosen vector that has complementary cohesive termini. Alternatively, the ends of the DNA molecules may be enzymatically modified or any site may be produced by ligating nucleotide sequences (linkers) into the DNA termini. Such vectors may be engineered to contain selectable marker genes that provide for the selection of cells. Such markers allow identification and/or selection of host cells that express the proteins encoded by the marker.

Additional vectors include lipoplexes (cationic liposome-DNA complex), polyplexes (cationic polymer-DNA complex), and protein-DNA complexes. In addition to a nucleic acid, a vector may also comprise one or more regulatory regions, and/or selectable markers useful in selecting, measuring, and monitoring nucleic acid transfer results (transfer to which tissues, duration of expression, etc.).

The term "plasmid" refers to an extra-chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. As used herein, the term "plasmid" refers to a construct made up of genetic material (i.e., nucleic acids). Typically a plasmid contains an origin of replication which is functional in bacterial host cells, e.g., *Escherichia coli*, and selectable markers for detecting bacterial host cells comprising the plasmid.

Plasmids of the present invention may include genetic elements as described herein arranged such that an inserted coding sequence can be transcribed and translated in eukaryotic cells. In certain embodiments described herein, a plasmid is a closed circular DNA molecule.

The term "expression" refers to the biological production of a product encoded by a coding sequence. In most cases a DNA sequence, including the coding sequence, is transcribed to form a messenger-RNA (mRNA). The messenger-RNA is then translated to form a polypeptide product which has a relevant biological activity. Also, the process of expression may involve further processing steps to the RNA product of transcription, such as splicing to remove introns, and/or post-translational processing of a polypeptide product.

The term "expression vector" refers to a vector, plasmid or vehicle designed to enable the expression of an inserted nucleic acid sequence following transformation into the host. The cloned gene, i.e., the inserted nucleic acid sequence, e.g., a HGF gene or variant thereof, is usually placed under the control of control elements such as a promoter, a minimal promoter, an enhancer, or the like. Initiation control regions or promoters, which are useful to drive expression of a nucleic acid in the desired host cell are numerous and familiar to those skilled in the art. Virtually any promoter capable of driving expression of these genes can be used in an expression vector, including but not limited to, viral promoters, bacterial promoters, animal promoters, mammalian promoters, synthetic promoters, constitutive promoters, tissue specific promoters, pathogenesis or disease related promoters, developmental specific promoters, inducible promoters, light regulated promoters; including, but are not limited to, the SV40 early (SV40) promoter region, the promoter contained in the 3' long terminal repeat (LTR) of Rous sarcoma virus (RSV), the E1A or major late promoter (MLP) of adenoviruses (Ad), the human cytomegalovirus (HCMV) immediate early promoter, the herpes simplex virus (HSV) thymidine kinase (TK) promoter, the baculovirus IE1 promoter, the elongation factor 1 alpha (EF1) promoter, the glyceraldehyde-3-phosphate dehydrogenase (GAPDH) promoter, the phosphoglycerate kinase (PGK) promoter, the ubiquitin C (Ubc) promoter, the albumin promoter, the regulatory sequences of the mouse metallothionein-L promoter and transcriptional control regions, the ubiquitous promoters (HPRT, vimentin, β-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis or disease related-promoters, and promoters that exhibit tissue specificity and have been utilized in transgenic animals, such as the elastase I gene control region which is active in pancreatic acinar cells; insulin gene control region active in pancreatic beta cells, immunoglobulin gene control region active in lymphoid cells, mouse mammary tumor virus control region active in testicular, breast, lymphoid and mast cells; albumin gene, Apo AI and Apo AII control regions active in liver, alpha-fetoprotein gene control region active in liver, alpha 1-antitrypsin gene control region active in the liver, beta-globin gene control region active in myeloid cells, myelin basic protein gene control region active in oligodendrocyte cells in the brain, myosin light chain-2 gene control region active in skeletal muscle, and gonadotropic releasing hormone gene control region active in the hypothalamus, pyruvate kinase promoter, villin promoter, promoter of the fatty acid binding intestinal protein, promoter of the smooth muscle cell β-actin, and the like. In addition, these expression sequences may be modified by addition of enhancer or regulatory sequences and the like. Non-limiting examples of expression vectors of the invention include pCK (Lee et al., *Biochem. Biophys. Res. Commun.* 272:230 (2000); WO 2000/040737) and pCP (pCDNA3.1, Invitrogen, USA).

A "construct" as used herein generally denotes a composition that does not occur in nature. A construct can be produced by synthetic technologies, e.g., recombinant DNA preparation and expression or chemical synthetic techniques for nucleic or amino acids. A construct can also be produced by the addition or affiliation of one material with another such that the result is not found in nature in that form.

A "gene" refers to a polynucleotide comprising nucleotides that encode a functional molecule, including functional molecules produced by transcription only (e.g., a bioactive RNA species) or by transcription and translation (e.g., a polypeptide). The term "gene" encompasses cDNA and genomic DNA nucleic acids. "Gene" also refers to a nucleic acid fragment that expresses a specific RNA, protein or polypeptide, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and/or coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A chimeric gene may comprise coding sequences derived from different sources and/or regulatory sequences derived from different sources. "Endogenous gene" refers to a native gene in its natural location in the genome of an organism. A "foreign" gene or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the cell by a gene transfer procedure.

"Heterologous DNA" refers to DNA not naturally located in the cell, or in a chromosomal site of the cell. The heterologous DNA may include a gene foreign to the cell.

The phrases "isolated" or "biologically pure" refer to material that is substantially or essentially free from components which normally accompany the material as it is found in its native state. Thus, isolated peptides in accordance with the invention preferably do not contain materials normally associated with the peptides in their in situ environment.

Lyophilized DNA Formulations

The DNA formulation of the invention, prior to lyophilization, is formulated with certain excipients, including a carbohydrate and a salt.

As described herein, the stability of a lyophilized formulation of DNA to be utilized as a diagnostic or therapeutic agent can be increased by formulating the DNA prior to lyophilization with an aqueous solution comprising a stabilizing amount of carbohydrate.

A carbohydrate of the DNA formulation of the invention is a mono-, oligo-, or polysaccharide, such as sucrose, glucose, lactose, trehalose, arabinose, pentose, ribose, xylose, galactose, hexose, idose, mannose, talose, heptose, fructose, gluconic acid, sorbitol, mannitol, methyl a-glucopyranoside, maltose, isoascorbic acid, ascorbic acid, lactone, sorbose, glucaric acid, erythrose, threose, allose, altrose, gulose, erythrulose, ribulose, xylulose, psicose, tagatose, glucuronic acid, galacturonic acid, mannuronic acid, glucosamine, galactosamine, neuraminic acid, arabinans, fructans, fucans, galactans, galacturonans, glucans, mannans, xylans, levan, fucoidan, carrageenan, galactocarolose, pectins, pectic acids, amylose, pullulan, glycogen, amylopectin, cellulose, dextran, cyclodextrin, pustulan, chitin, agarose, keratin, chondroitin, dermatan, hyaluronic acid, alginic acid, xantham gum, or starch.

In one aspect, the carbohydrate is mannitol or sucrose.

The carbohydrate solution prior to lyophilization can correspond to carbohydrate in water alone, or a buffer can be included. Examples of such buffers include PBS, HEPES, TRIS or TRIS/EDTA. Typically the carbohydrate solution is combined with the DNA to a final concentration of about 0.05% to about 30% sucrose, typically 0.1% to about 15% sucrose, such as 0.2% to about 5%, 10% or 15% sucrose, preferably between about 0.5% to 10% sucrose, 1% to 5% sucrose, 1% to 3% sucrose, and most preferably about 1.1% sucrose.

A salt of the DNA formulation of the invention is NaCl or KCl. In certain aspects, the salt is NaCl. In further aspects, the salt of the DNA formulation is in an amount selected from the group consisting of between about 0.001% to about 10%, between about 0.1% and 5%, between about 0.1% and 4%, between about 0.5% and 2%, between about 0.8% and 1.5%, between about 0.8% and 1.2% w/v. In certain embodiments, the salt of the DNA formulation is in an amount of about 0.9% w/v.

In the DNA formulation of the invention, the final concentration of DNA is from about 1 ng/mL to about 30 mg/mL of plasmid. For example, a formulation of the present invention may have a final concentration of about 1 ng/mL, about 5 ng/mL, about 10 ng/mL, about 50 ng/mL, about 100 ng/mL, about 200 ng/mL, about 500 ng/mL, about 1 µg/mL, about 5 µg/mL, about 10 µg/mL, about 50 µg/mL, about 100 µg/mL, about 200 µg/mL, about 400 µg/mL, about 500 µg/mL, about 600 µg/mL, about 800 µg/mL, about 1 mg/mL, about 2 mg/mL, about 2.5 mg/mL, about 3 mg/mL, about 3.5 mg/mL, about 4 mg/mL, about 4.5 mg/mL, about 5 mg/mL, about 5.5 mg/mL, about 6 mg/mL, about 7 mg/mL, about 8 mg/mL, about 9 mg/mL, about 10 mg/mL, about 20 mg/mL, or about 30 mg mg/mL of a plasmid. In certain embodiments of the invention, the final concentration of the DNA is from about 100 µg/mL to about 2.5 mg/mL. In particular embodiments of the invention, the final concentration of the DNA is from about 0.5 mg/mL to 1 mg/mL.

The DNA formulation of the invention is lyophilized under standard conditions known in the art. A method for lyophilization of the DNA formulation of the invention may comprise (a) loading a container, e.g., a vial, with a DNA formulation, e.g., a DNA formulation comprising a plasmid DNA, a salt and a carbohydrate, where the plasmid DNA comprises an HGF gene, or variant thereof, into a lyophilizer, wherein the lyophilizer has a starting temperature of about 5° C. to about −50° C.; (b) cooling the DNA formulation to subzero temperatures (e.g., −10° C. to −50° C.); and (c) substantially drying the DNA formulation. The conditions for lyophilization, e.g., temperature and duration, of the DNA formulation of the invention can be adjusted by a person of ordinary skill in the art taking into consideration factors that effect lyophilization parameters, e.g., the type of lyophilization machine used, the amount of DNA used, and the size of the container used.

The container holding the lyophilized DNA formulation may then be sealed and stored for an extended period of time at various temperatures (e.g., room temperature to about −180° C., preferably about 2-8° C. to about −80° C., more preferably about −20° C. to about −80° C., and most preferably about −20° C.). In certain aspects, the lyophilized DNA formulations are preferably stable within a range of from about 2-8° C. to about −80° C. for a period of at least 6 months without losing significant activity. Stable storage plasmid DNA formulation can also correspond to storage of plasmid DNA in a stable form for long periods of time before use as such for research or plasmid-based therapy. Storage time may be as long as several months, 1 year, 5 years, 10 years, 15 years, or up to 20 years. Preferably the preparation is stable for a period of at least about 3 years.

HGF Plasmid DNA

The present invention provides for a lyophilized DNA formulation, where the DNA formulation, prior to lyophilization, comprises a plasmid DNA, and the plasmid DNA comprises an HGF gene, or variant thereof.

Hepatocyte growth factor (HGF) is a heparin binding glycoprotein also known as scatter factor or hepatopoietin-A. An endogenous gene encoding human HGF is located at chromosome 7q21.1 and comprises 18 exons and 17 introns, having the nucleotide sequence of SEQ ID NO: 1 (Seki T., et al., *Gene* 102:213-219 (1991)). A transcript of about 6 kb is transcribed from the HGF gene, and then, a polypeptide HGF precursor consisting of 728 amino acids (SEQ ID NO: 2) is synthesized therefrom. Simultaneously, a polypeptide of dHGF precursor consisting of 723 amino acids is also synthesized by an alternative splicing of the HGF gene. The biologically inactive precursors may be converted into active forms of disulfide-linked heterodimer by protease in serum. In the heterodimers, the alpha chain having a high molecular weight forms four kringle domains and an N-terminal hairpin loop like a preactivated peptide region of plasminogen. The kringle domains of a triple disulfide-bonded loop structure consisting of about 80 amino acids may play an important role in protein-protein interaction. The low molecular weight beta chain forms an inactive serine protease-like domain. dHGF consisting 723 amino acids is a polypeptide with deletion of five amino acids in the 1st kringle domain of the alpha chain, i.e., F, L, P, S and S.

HGF secreted from mesoderm-derived cells has various biological functions, e.g., 1) inducing epithelial cells into a tubular structure; 2) stimulating vascularization from endothelial cells in vitro and in vivo; 3) regeneration of liver and kidney, owing to its anti-apoptosis activity; 4) organogenesis of kidney, ovary and testis; 5) controlling osteogenesis; 6) stimulating the growth and differentiation of erythroid hematopoietic precursor cells; and 7) axon sprouting of neurons (Stella, M. C. and Comoglio, P. M., *The International Journal of Biochemistry & Cell Biology* 31:1357-1362 (1999)). Based on these various functions, HGF or a gene encoding HGF or a variant thereof, may be developed as a therapeutic agent for treating ischemic or liver diseases. Actually, in vivo, the HGF may exist as either HGF or dHGF, and therefore, the coexpression of HGF and dHGF is important for maximizing the therapeutic effect. A hybrid HGF gene which can simultaneously express HGF and dHGF with a high efficiency for gene therapy is an HGF variant that would be advantageous to utilize in the plasmid DNA formulation of the present invention.

The hybrid HGF gene has been previously described in Intl. Appl. No. WO 03/078568 and U.S. Publ. No, 2005/0079581 A1, the contents of each which are herein incorporated by reference. The hybrid HGF gene is prepared by inserting an inherent or foreign intron between exons 4 and 5 in HGF cDNA. The hybrid HGF gene has a higher expression efficiency than HGF cDNA and simultaneously expresses two heterotypes of HGF and dHGF (deleted variant HGF).

The term "isoform of HGF" refers to any HGF polypeptide having an amino acid sequence that is at least 80% identical (e.g., at least 90% or 95% identical) to a HGF amino acid sequence that is naturally produced in an animal, including all allelic variants. In one embodiment, the term refers to isoforms that are known to have cell proliferation activity. Isoforms of HGF include, without limitation, flHGF, dHGF, NK1, NK2, and NK4, e.g., corresponding to SEQ ID NOs: 2-6, and variants thereof (e.g., NK2 variants, SEQ ID NOs: 11-12).

The term "flHGF" refers to the full length HGF protein of an animal, e.g., a mammal, e.g., amino acids 1-728 (SEQ ID NO: 2) of human HGF.

The term "dHGF" refers to the deleted variant of HGF protein produced by alternative splicing of the HGF gene in an animal, e.g., a mammal, e.g., human HGF consisting of 723 amino acids (SEQ ID NO: 3) with deletion of five amino acids in the 1st kringle domain of the alpha chain (F, L, P, S and S) from the full length HGF sequence.

The term "NK1" refers to an isoform of HGF from an animal, e.g., a mammal, e.g., a human, consisting of the N-terminal hairpin loop and kringle1 domains.

The term "NK2" refers to an isoform of HGF from an animal, e.g., a mammal, e.g., a human, consisting of the N-terminal hairpin loop, kringle1, and kringle2 domains.

The term "NK4" refers to an isoform of HGF from an animal, e.g., a mammal, e.g., a human, consisting of the N-terminal hairpin loop, kringle1, kringle2, kringle3, and kringle4 domains.

The structure and function of HGF has been extensively studied and one of skill in the art is aware of the amino acids in the HGF sequence that are important for retaining substantially all of the biological activity of the protein and that are preferably not changed or only conservatively changed in any sequence variant of HGF. See, e.g., Hartmann et al., *Proc. Natl. Acad. Sci. USA* 89:11574 (1992); Lokker et al., *EMBO J.* 11:2503 (1992), Zhou et al., *Structure* 6:109 (1998), Ultsch et al., *Structure* 6:1383 (1998), Shimizu et al., *Biochem. Biophys. Res. Commun.* 189:1329 (1992), Yoshiyama et al., *Biochem. Biophys. Res. Commun.* 175:660 (1991), each herein incorporated by reference in its entirety. For example, it appears that the N-terminal hairpin loop and kringle1 domains are required for cell proliferation activity. Other amino acids that are not critical to biological activity may be deleted and/or substituted more freely. One of skill in the art can prepare variants of HGF isoforms using routine mutagenesis techniques, such as those described in the references cited above, and identify variants retaining substantially all of the biological activity of the HGF isoform.

An embodiment of the hybrid HGF gene of the present invention comprising the inherent intron is 7113 by long and has the nucleotide sequence of SEQ ID NO: 7.

A hybrid HGF gene may comprise a fragment of inherent intron optionally having a small recombinant sequence inserted thereinto between exons 4 and 5 of HGF cDNA. Herein, such a hybrid HGF gene comprising a fragment of inherent intron is designated "HGF-X". Examples of hybrid HGF genes include HGF-X2 (SEQ ID NO: 13), HGF-X3 (SEQ ID NO: 14), HGF-X6 (SEQ ID NO: 8), HGF-X7 (SEQ ID NO: 9) and HGF-X8 (SEQ ID NO: 10).

Administration and Methods of Treatment

As described above, HGF has various biological functions, and based on these various functions, HGF, a gene encoding HGF, or a variant thereof, may be developed as a therapeutic agent for treating ischemic or liver diseases. In the present invention, an HGF DNA formulation is administered after reconstitution of the lyophilized DNA formulation.

The term "reconstituted" or "reconstitution" refers to the restoration to the original form, e.g., by rehydration, of a substance previously altered for preservation and storage, e.g., the restoration to a liquid state of a DNA plasmid formulation that has been previously dried and stored. The lyophilized composition of the present invention may be reconstituted in any aqueous solution which produces a stable, mono-dispersed solution suitable for administration. Such aqueous solutions include, but are not limited to: sterile water, TE, PBS, Tris buffer or normal saline.

The concentration of reconstituted lyophilized DNA in the methods of the current invention is adjusted depending on many factors, including the amount of a formulation to be delivered, the age and weight of the subject, the delivery method and route and the immunogenicity of the antigen being delivered.

The reconstituted lyophilized DNA formulation of the invention may be administered orally or via parenteral routes such as intravenous, intramuscular, intraendocardial, intramyocardial, intrapericardial, intraventricular, intraarticular, intradermal, intracerebral, intrarenal, intrahepatic, intrasplenic, intralymphatic, subcutaneous, intraabdominal, intratesticular, intraovarian, intrauterine, sternal, intratracheal, intraplueral, intrathoracic, intradural, intraspinal, intramedullary, intramural, intrascorionic and arterial injection or infusion, or topically through rectal, intranasal, inhalational or intraocular administration. In certain embodiments, the method of delivery is intramuscular, intramyocardial, intravenous, intracerebral, or intrarenal.

It should be understood that the typical daily dose of the reconstituted lyophilized DNA formulation of the present invention ought to be determined in light of various relevant factors including the conditions to be treated, the chosen route of administration, the age, sex and body weight of the individual patient, and the severity of the patient's symptom, and can be administrated in a single dose or in divided dose. Therefore, the daily dose should not be construed as a limitation to the scope of the invention in any way.

The term "treat," "treating," or "treatment" of an ischemic or liver disease, as used herein, refers to the administration to a subject of a factor, e.g. a HGF, e.g., a hybrid HGF, or variant thereof, in an amount sufficient to result in amelioration of one or more symptoms of the ischemic or liver disease, or prevent advancement of the ischemic or liver disease.

An "ischemic disease" refers to a disease associated with a deficient supply of blood to a body part (as the heart or brain) that is due to obstruction of the inflow of arterial blood (as by the narrowing of arteries by spasm or disease). Examples of ischemic diseases include coronary artery disease (CAD) and peripheral artery disease (PAD).

The term "liver disease" applies to many diseases and disorders that cause the liver to function improperly or cease functioning. HGF is a major agent promoting hepatocyte proliferation, and acts in concert with transforming growth factor-alpha and heparin-binding epidermal growth factor during liver regeneration. Additionally, HGF ameliorates hepatic injury via anti-apoptotic effects in animal models of fulminant hepatic failure, and attenuates hepatic fibrosis in animals with liver cirrhosis. Consequently, HGF is considered to not only induce liver regeneration, but also to inhibit disease progression and ameliorate hepatic fibrosis in patients suffering from intractable liver diseases. With respect to the treatment of liver disease, the reconstituted lyophilized DNA formulation of the invention may be administered according to the delivery methods as set forth above. In certain embodiments, the method of delivery in the treatment of liver disease will be intravenous, intraarterial, or intrahepatic.

In certain aspects of the invention, the reconstituted HGF DNA formulation can comprise two or more isoforms of HGF. The HGF isoforms may be previously lyophilized separately, or in the same DNA formulation. Both of these lyophilized isoforms, after reconstitution, can be administered separately or at the same time, i.e., co-administered; separate reconstituted plasmid DNA formulations for the two or more isoforms of HGF may be administered or co-administered or a single expression plasmid containing genes for two or more isoforms of HGF and capable of expressing the genes for the two or more isoforms of HGF may be administered. For example, the two isoforms flHGF and dHGF may be administered using two separate plasmids. Alternatively, the two separate plasmids containing genes for flHGF and dHGF may be used for co-administration. Finally, a single expression plasmid containing genes for both flHGF and dHGF may be administered. In certain aspects of the invention, the flHGF and dHGF on a single expression plasmid is encoded by the same polynucleotide or by separate polynucleotides.

There are a number of approaches to include more than one polynucleotide capable of expressing an HGF isoform on a single plasmid. These include, for example, the use of Internal Ribosome Entry Site (IRES) sequences, dual promoters/expression cassettes, and fusion proteins. The two or more isoforms expressed from the same plasmid or on two separate plasmids, as discussed above, are selected from the group consisting of flHGF, dHGF, NK1, NK2, and NK4 or selected from the group consisting of SEQ ID NOs: 2 to 6. The two or more isoforms can also include additional HGF isoforms known to one of ordinary skill in the art.

In certain aspects of the invention, the plasmid DNA is administered through direct intracellular injection and, more preferably, by the use of a syringe or a catheter. Catheters have been used to introduce recombinant genes in vivo (see, e.g., E. G. Nabel, et al., *Proc. Natl. Acad. Sci. USA* 89, 5157 (1992); E. G. Nabel, et al., *Science* 249, 1285 (1990); E. G. Nabel, et al., *Science* 244, 1342 (1989); E. G. Nabel, et al., *J. Clin. Invest.* 91, 1822 (1993); G. Plautz, et al., *Circ.* 83, 578 (1991); E. G. Nabel, et al., *Nature* (1993) (in press)). Utilization of a catheter provides the ability to deliver the plasmid DNA into the cells which are difficult to access by the use of a syringe.

The plasmid DNA can be administered through intraarterial or intravenous injection and, more preferably, by the use of a syringe or a catheter. For example, the femoral artery may be used to deliver plasmid DNA to the heart; the portal vein may be used to deliver plasmid DNA to the liver.

Administration of the plasmid DNA of the invention can also be accomplished by gene transfer into target cells, in situ, to optimize the subsequent delivery of genes in vivo.

The practice of the present invention will employ, unless otherwise indicated, conventional techniques of cell biology, cell culture, molecular biology (including PCR), vaccinology, microbiology, recombinant DNA, and immunology, which are within the skill of the art. Such techniques are explained fully in the literature. See, for example, *Molecular Cloning A Laboratory Manual*, 2nd Ed., Sambrook et al., ed., Cold Spring Harbor Laboratory Press: (1989); DNA Cloning, Volumes I and II (D. N. Glover ed., 1985); Oligonucleotide Synthesis (M. J. Gait ed., 1984); Mullis et al. U.S. Pat. No: 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); and in Ausubel et al., Current Protocols in Molecular Biology, John Wiley and Sons, Baltimore, Md. (1989). Each of the references cited in this paragraph is incorporated herein by reference in its entirety.

The following Examples are given for the purpose of illustration only, and are not intended to limit the scope of the invention.

EXAMPLES

Example 1

Preparation of Plasmid

The plasmid pCK-HGF-X7 (WO 03/078568) which is designed to express hepatocyte growth factor (HGF) protein was used in the experiment.

*E. coli* (TOP10, Invitrogen, USA) were transformed with pCK-HGF-X7, and a single colony was isolated. The isolated colony was then cultured in LB media containing 30 μg/mL kanamycin. Plasmid DNA was purified using an EndoFree plasmid Giga kit (Qiagen, USA), and re-suspended in saline containing 0.9% NaCl at a final DNA concentration of 1.0 to 2.0 mg/mL.

Example 2

Lyophilization

Formulations of pCK-HGF-X7 were prepared in saline containing 0.9% NaCl at a final DNA concentration of 0.5 mg/mL or 1 mg/mL, with sucrose (0.25, 1.1, 5, 10 or 20% w/v) or mannitol (1.2, 4.85 or 10% w/v). Table 1A and 1B show the percentage sucrose and mannitol, respectively, and the corresponding carbohydrate/DNA (w/w) ratios for the tested pCK-HGF-X7 formulations.

TABLE 1A

Percent Sucrose

| DNA (mg/ml) | Sucrose (%) | Sucrose (mg/ml)) | Sucrose to DNA ratio (w/w) |
|---|---|---|---|
| 0.5 | 0.25 | 2.5 | 5 |
| 0.5 | 1.1 | 11 | 22 |
| 0.5 | 5 | 50 | 100 |
| 0.5 | 10 | 100 | 200 |
| 0.5 | 20 | 200 | 400 |
| 1 | 0.25 | 2.5 | 2.5 |
| 1 | 1.1 | 11 | 11 |
| 1 | 5 | 50 | 50 |
| 1 | 10 | 100 | 100 |
| 1 | 20 | 200 | 200 |

TABLE 1B

Percent Mannitol

| DNA (mg/ml) | Mannitol (%) | Mannitol (mg/ml)) | Mannitol to DNA ratio (w/w) |
|---|---|---|---|
| 0.5 | 1.2 | 12 | 24 |
| 0.5 | 4.85 | 48.5 | 97 |
| 0.5 | 10 | 100 | 200 |
| 1 | 1.2 | 12 | 12 |
| 1 | 4.85 | 48.5 | 48.5 |
| 1 | 10 | 100 | 100 |

The suspended plasmid DNA was then lyophilized with Production-Master Freeze Dryer (C&H Cooling & Heating Systems, Korea). The temperature was lowered to −50° C. for 4 hours at 100 mTorr. Then, the temperature was raised to −40° C. for 12 hours, −30° C. for 6 hours, −20° C. for 6 hours, −10° C. for 6 hours, 0° C. for 6 hours, 10° C. for 6 hours and 30° C. for 24 hours, progressively, at 28~29 mTorr. The lyophilized plasmid DNA was kept at −20° C. until analyzed.

The suspended plasmid DNA was also lyophilized with Production-Master Freeze Dryer (C&H Cooling & Heating Systems, Korea). The temperature was lowered to 5° C. for 1 minute, and −50° C. for 2 hours at 100 mTorr. Then, the temperature was raised to −40° C. for 6 hours, −35° C. for 3 hours, −30° C. for 6 hours, −25° C. for 3 hours, −20° C. for 3 hours, −15° C. for 3 hours, −10° C. for 6 hours, −5° C. for 3 hours, 0° C. for 6 hours, and 30° C. for 17 hours, progressively, at 28~29 mTorr. The lyophilized plasmid DNA was kept at −20° C. until analyzed.

The suspended plasmid DNA was also lyophilized with Production-Master Freeze Dryer (C&H Cooling & Heating Systems, Korea). The temperature was lowered to 5° C. for 1 minute, −10° C. for 1 minute, −20° C. for 1 minute, −30° C. for 1 minute, and −50° C. for 1 minute at 150 mTorr. The temperature was maintained at −50° C. for another 2 hours at 150 mTorr. Then, the temperature was raised to −45° C. for 6 hours, −40° C. for 3 hours, −35° C. for 6 hours, −30° C. for 3 hours, −25° C. for 6 hours, −20° C. for 3 hours, −15° C. for 6 hours, −10° C. for 3 hours, −5° C. for 6 hours, 0° C. for 12 hours, 10° C. for 3 hours, 20° C. for 6 hours, and 30° C. for 29 hours, progressively, at 30 mTorr. The lyophilized plasmid DNA was kept at −20° C. until analyzed.

The lyophilized formulations prepared above were analyzed for in vitro gene expression efficiency according to the methods described in Example 3. The in vitro results for these preparations were the same.

Example 3

Effects of Lyophilization on In Vitro Gene Expression Efficiency of Plasmid DNA

1. Materials and Methods

To assess the effects of the lyophilization on gene expression efficiency of plasmid DNA, the lyophilized plasmid DNA was transfected into 293T cells, and the level of HGF expression was measured. As a control, non-lyophilized plasmid DNA was also transfected.

Four micrograms of pCK-HGF-X7 in various formulations (as noted above in Example 1) were transfected into $1 \times 10^6$ 293T cells using FuGENE6 (Roche Diagnostics, Germany) (n=5). Before transfection, 1 mg of the lyophilized plasmid DNA was reconstituted with 2 ml of water for injection to the final concentration of 0.5 mg/mL.

Two days after transfection, the culture supernatants were obtained and analyzed for HGF expression using a human HGF ELISA kit (R&D Systems, MN, USA), according to the manufacturer's recommendations. The ELISA results were statistically assessed by Dunnett's multiple comparison test using SPSS program (version 13.0, SPSS. Inc, USA).

2. Results and Discussion

The results of HGF gene expression are provided in FIG. 1. Contrary to previous reports, lyophilization did not affect the in vitro gene expression efficiency of plasmid DNA. Among various formulations, the HGF level from pCK-HGF-X7 lyophilized with 1.1% sucrose and 0.9% NaCl was significantly higher than that from non-lyophilized pCK-HGF-X7 (p=0.001) (FIG. 1).

These results indicate that the lyophilization formulation containing 1.1% Sucrose and 0.9% NaCl would be more suitable for pCK-HGF-X7 than a non-lyophilized formulation.

Example 4

Comparative Analysis of In Vivo Gene Expression Between Non-Lyophilized and Lyophilized pCK-HGF-X7

1. Materials and Methods

Thirteen 5-week old BALB/c mice (males, Charles River) were obtained for each group, and provided with food and water ad libitum. The mice were allowed 7 days of rest before being subjected to the experiment.

Mice were injected with 100 μg of non-lyophilized pCK-HGF-X7 containing 0.9% NaCl (NL-HGF-X7) or pCK-HGF-X7 lyophilized with 1.1% sucrose and 0.9% NaCl (L-HGF-X7) into the tibialis cranialis, and were sacrificed at day 7 after treatment. The lyophilized plasmid DNA was reconstituted with water to the final concentration of 0.5 mg/mL before injection. To measure the level of HGF protein expression, the injected muscles were collected, and the muscle tissue was lysed with 500 μL of cell lysis buffer (50 mM NaCl, 0.2% sodium dodecyl sulfate, 0.5% sodium deoxycholate, 2% IGEPAL CA-630, 25 mM Tris-HCl, pH7.4, 1 mM phenylmethylsulfonyl fluoride) for 16 hours at 4° C. The lysates were centrifuged at 12,000 rpm for 5 minutes, and the supernatants were harvested and analyzed for HGF expression using a human HGF ELISA kit (R&D Systems).

The ELISA results were statistically assessed by one way ANOVA and subsequent Tukey's Test using SPSS program (version 13.0).

2. Results and Discussion

Figure 2:
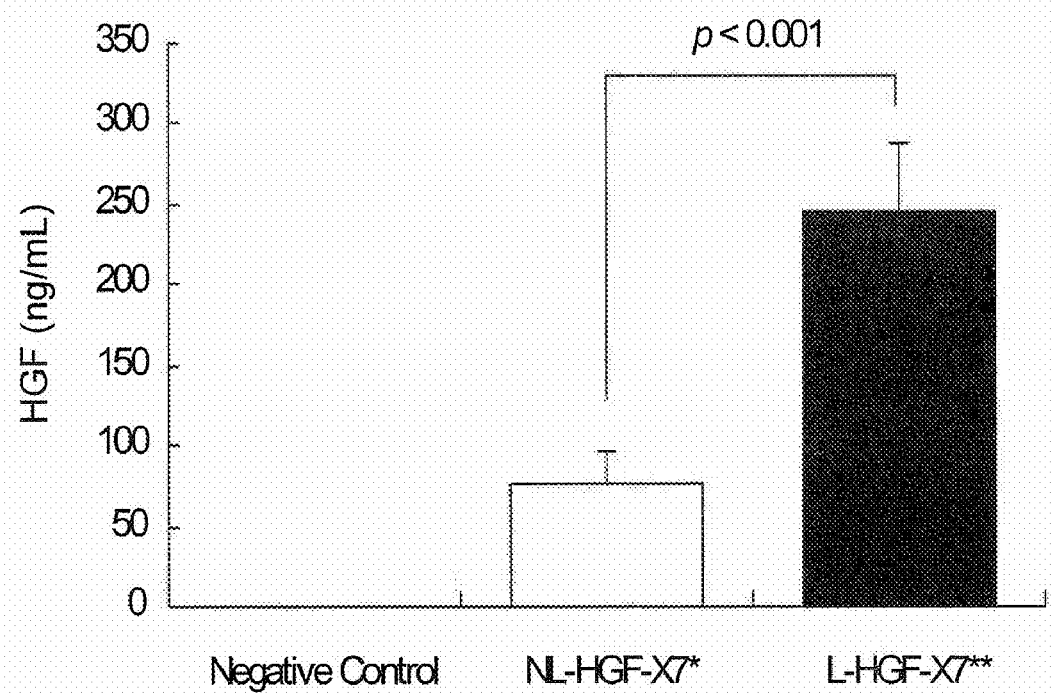
FIG. 2 depicts a bar graph comparing in vivo HGF expression between non-lyophilized and lyophilized pCK-HGF-X7. Mice were injected with 100 µg of non-lyophilized pCK-HGF-X7 containing 0.9% NaCl (NL-HGF-X7) or pCK-HGF-X7 lyophilized with 1.1% Sucrose and 0.9% NaCl (L-HGF-X7) into the tibialis cranialis. HGF expression levels were measured using ELISA in muscle tissue lysates after sacrificing the mice at day 7. HGF expression levels are shown for negative control (lane 1), non-lyophilized pCK-HGF-X7 containing 0.9% NaCl (NL-HGF-X7; lane 2), and pCK-HGF-X7 lyophilized with 1.1% sucrose and 0.9% NaCl (L-HGF-X7; lane 3).

An average of 246 ng/mL of HGF protein was produced from the animals administered with pCK-HGF-X7 lyophilized with 1.1% sucrose and 0.9% NaCl (L-HGF-X7), while the animals administered with non-lyophilized pCK-HGF-X7 expressed 76 ng/mL of HGF (FIG. 2). This result indicates that pCK-HGF-X7 lyophilized with 1.1% sucrose and 0.9% NaCl can express HGF protein more efficiently than non-lyophilized pCK-HGF-X7 (p <0.001).

Example 5

Comparative Analysis of Therapeutic Effects on Porcine Ischemic Heart Disease Model Between Non-Lyophilized and Lyophilized pCK-HGF-X7

1. Materials and Methods (1) Animals

Figure 3:
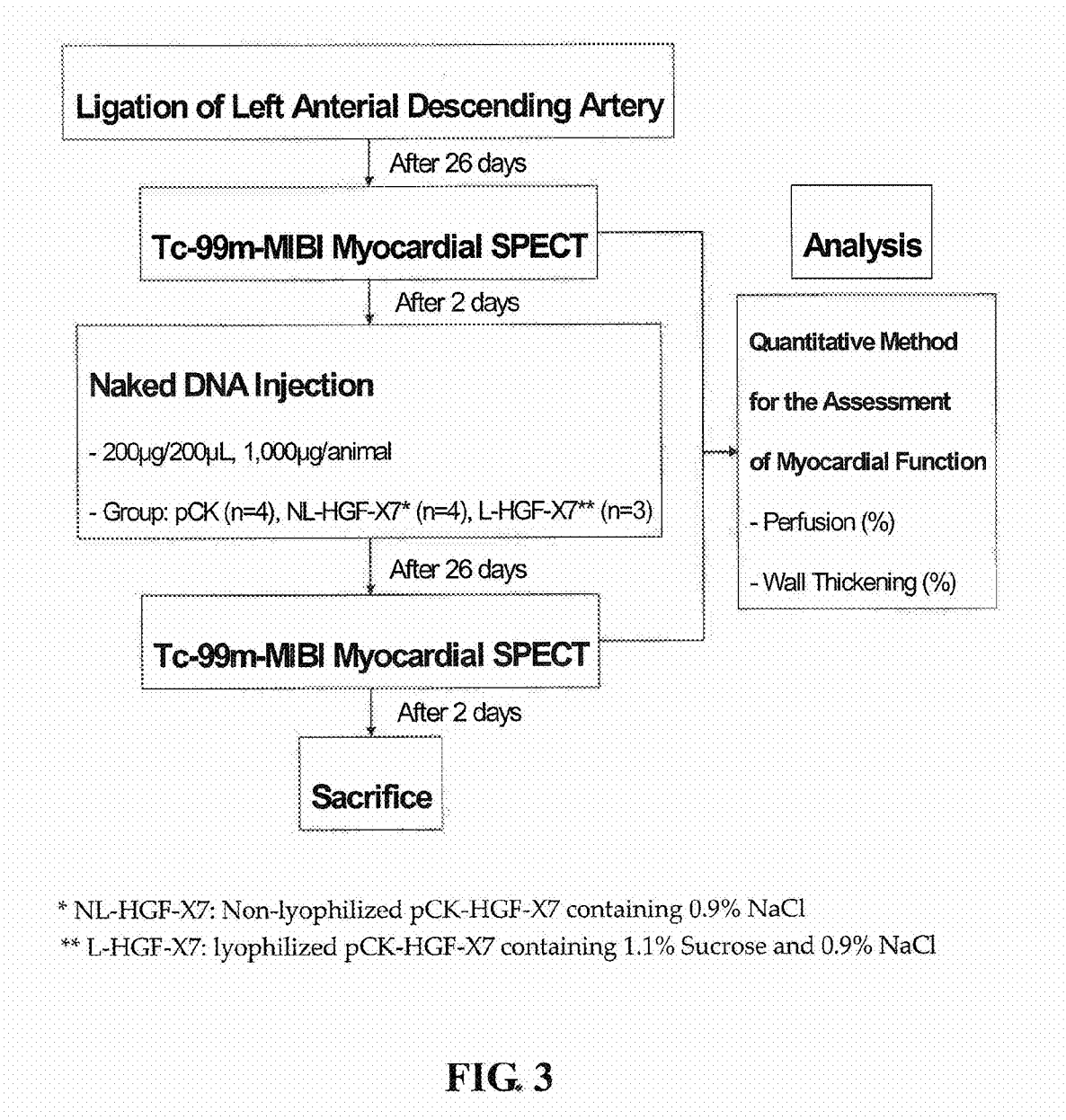
FIG. 3 shows a schematic diagram of the experimental procedure using the porcine ischemic heart disease model. NL-HGF-X7 corresponds to non-lyophilized pCK-HGF-X7 containing 0.9% NaCl. L-HGF-X7 corresponds to pCK-HGF-X7 lyophilized with 1.1% sucrose and 0.9% NaCl.

Eleven Yorkshire pigs (male, 28 to 30 kg, Clinical Research Institute in Seoul National University Hospital) were obtained and provided with food two-times per day and water ad libitum. The pigs were allowed 7 days of rest before being subjected to the experiment. The overall experimental plan is shown in FIG. 3.

2) Establishment of the Porcine Ischemic Heart Disease Model

Xylazine (2 mg/kg), ketamine (20 mg/kg), and atropine (0.05 mg/kg) were injected intramuscularly into each pig. Twenty minutes later, a 22-gauge Medicut sheath was inserted into the superficial femoral artery for continuous monitoring of the blood pressure. Thiopental sodium (10 mg/kg) was injected intravenously, and endotracheal intubation was performed via the orotracheal route. Anesthesia was maintained by inhalation of enflurane. During the operation, positive pressure ventilation and an oxygen fraction of 30%~40% were maintained. Electrocardiograms, oxygen saturation and arterial blood pressure were monitored continuously.

Left thoracotomy was then performed. After opening the pericardium followed by exploration of the left anterior descending coronary artery (LAD), 2% lidocaine (1 mg/kg) was injected intravenously and the distal one third of the LAD was ligated for 3 minutes, leaving the second diagonal branch as much as possible. Reperfusion (ischemic preconditioning)

was performed for 5 minutes using 5-0 polypropylene sutures buttressed with a small piece of Nelaton (4 Fr). After this single ischemic preconditioning, the distal LAD was ligated and ST-segment depression or elevation on the monitored electrocardiogram was confirmed. Additional lidocaine (1 mg/kg) was injected intravenously 15 minutes after the ligation, and the pericardium and thoracotomy wounds were closed. A single 28 Fr chest tube connected to wall suction was removed immediately after enough spontaneous respiration returned, followed by the removal of the endotracheal tube.

All protocols were approved by the Seoul National University Animal Care and Use Committee.

(3) Intramyocardial Injection of Plasmids

Twenty eight days after the ligation of the coronary artery, re-thoracotomy was performed. Using 27 gauge insulin injection needles, a total dose of 1 mg of pCK-HGF-X7 lyophilized with 1.1% sucrose and 0.9% NaCl (L-HGF-X7, n=3) or non-lyophilized pCK-HGF-X7 containing 0.9% NaCl (NL-HGF-X7, n=4) was injected into the anterolateral ischemic border zone which lies between the fibrotic infarction area and the grossly normal myocardium along the course of the second diagonal branch. A total of five sites were injected. Each site was injected with 0.2 mg of plasmid DNA and the interval between injection sites was 1.5 cm. The lyophilized plasmid DNA was reconstituted with water to the final concentration of 1 mg/mL before injection. As a control, the identical amount of non-lyophilized pCK containing 0.9% NaCl (n=4) was injected into the anterolateral ischemic border zone. The injection points were marked with suture tags using metal rings.

(4) Myocardial Single Photon Emission Computed Tomography

Twenty six days after the surgical induction of myocardial infarction, $^{99m}$Tc-MIBI gated single photon emission computed tomography (SPECT) (Vertex EPIC, ADAC Labs, CA., USA) was performed to set a baseline before plasmid injection. The gated SPECT was repeated 28 days later (on Day 54 after the induction of the myocardial infarction).

A 20-segment model was chosen for a segmental analysis. Six segments corresponding to the cardiac base were excluded from the analysis because this region could be easily influenced by the diaphragmatic attenuation or some artifacts around the heart; also because the heart base was far away from the sites of the distal coronary ligation and plasmid injection.

The SPECT images constructed by electrocardiography gating were analyzed by an auto-quantitation program (AutoQUANT, ADAC Labs, CA., USA), which is believed to eliminate the possible bias by any associated technician's manipulation.

The amount of segmental perfusion was quantified by measuring the uptake of $^{99m}$Tc-MIBI and calculated as a percentage of the maximum uptake. When the segmental perfusion thus estimated was less than 70%, it was defined as an underperfused segment and used as the target of plasmid delivery. Segments remaining well perfused even after the coronary ligation were also excluded, as they would probably get no benefit from the therapeutic angiogenesis. Wall thickening in the systolic phase was indicated as a percentage of the end diastolic wall thickness on the gated images.

(5) Statistics

Data are presented as the percent improvement compared to the baseline. All data were analyzed using SPSS (version 13.0). The statistical analysis of the myocardial perfusion and the segmental wall-thickening was performed using paired-samples Student t-test.

2. Results

Figure 4:
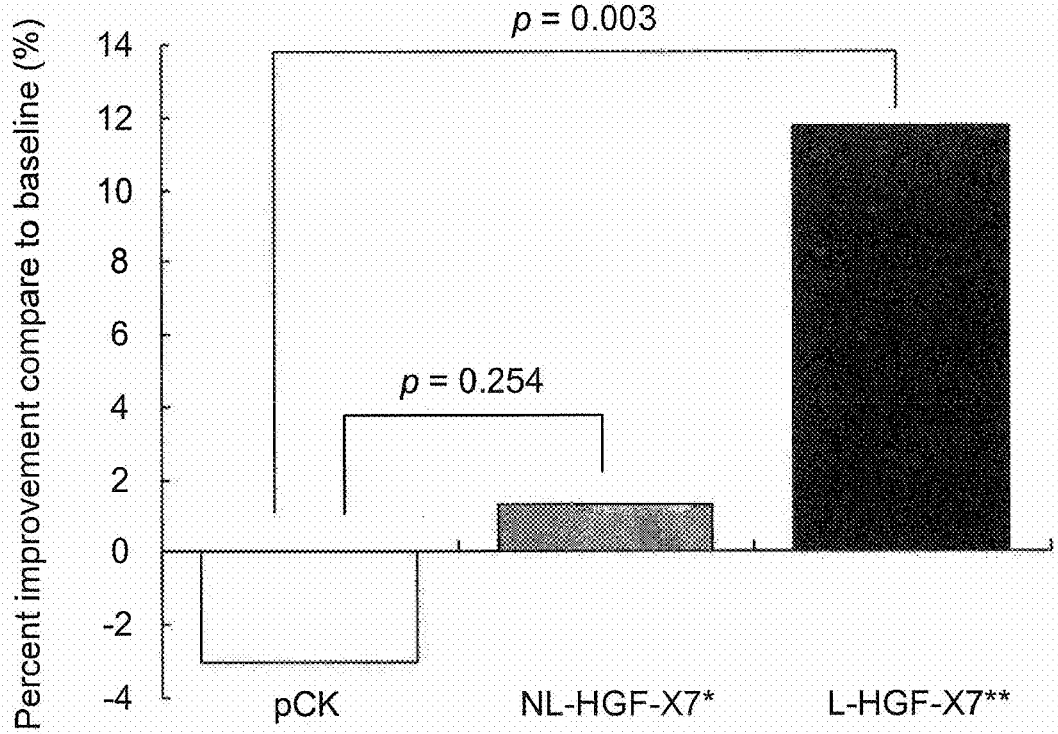
FIG. 4 depicts a bar graph showing the effect of non-lyophilized and lyophilized pCK-HGF-X7 on myocardial perfusion. The percent improvement of myocardial perfusion as compared to baseline is shown when the porcine ischemic heart disease model is utilized. Results are shown for pigs injected with plasmid alone (pCK; lane 1), non-lyophilized pCK-HGF-X7 containing 0.9% NaCl (NL-HGF-X7; lane 2), and pCK-HGF-X7 lyophilized with 1.1% sucrose and 0.9% NaCl (L-HGF-X7; lane 3).

Within each treatment group, the changes in the segmental perfusion before and after the plasmid DNA injection were compared. The baseline values for the average of segmental perfusion measured on Day 26 after LAD ligation were 39.0±14.6, 43.4±13.4 and 36.9±16.3% for pCK, NL-HGF-X7 and L-HGF-X7 treatment group, respectively. $^{99m}$Tc-MIBI gated SPECT conducted on Day 54 showed that the average values of the segmental perfusion in the pCK and NL-HGF-X7 groups were 37.8±13.9% and 44.0±14.5%, respectively, which were not significantly different from the baseline values measured on Day 26 (p=0.320 for pCK and 0.721 for NL-HGF-X7). In contrast, the average value of the segmental perfusion in the L-HGF-X7 treatment group was 41.2±17.6%, showing significant increase over the baseline value (p=0.003). When the magnitude of the percent increase in the segmental perfusion from baseline value was compared between groups, the percent increase of the segmental perfusion in the L-HGF-X7 treatment group was 14.74% higher than that of pCK treatment group (p=0.003), while the NL-HGF-X7 treatment group did not show significant difference from the pCK treatment group (p=0.254) (FIG. 4).

Figure 5:
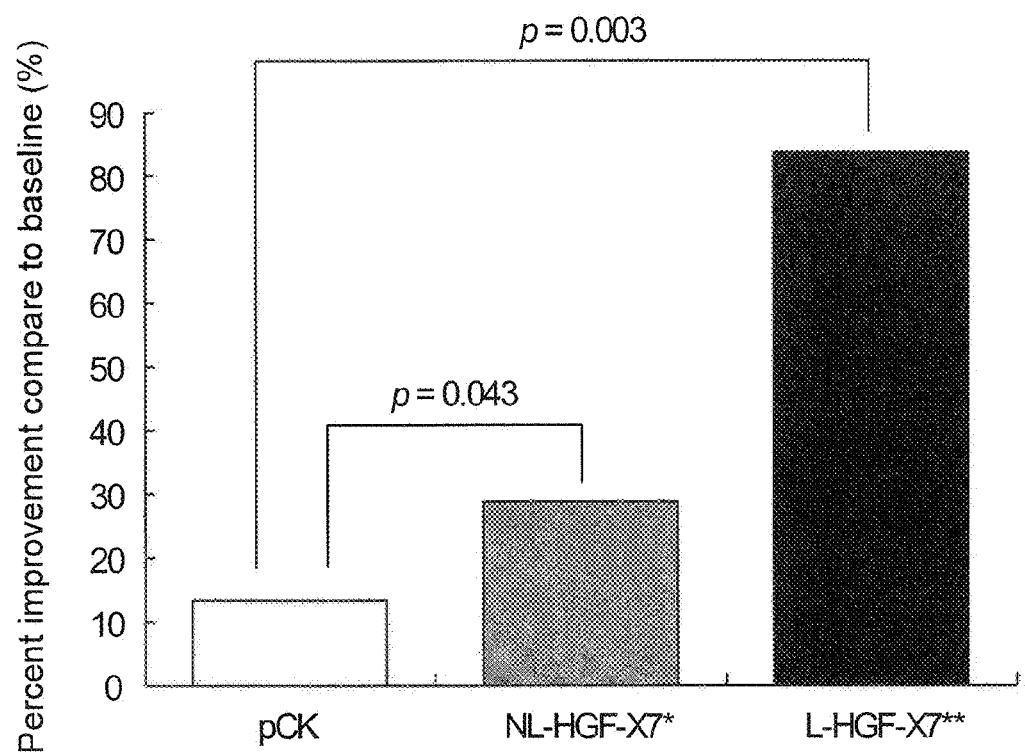
FIG. 5 depicts a bar graph showing the effect of non-lyophilized and lyophilized pCK-HGF-X7 on wall thickening. The percent improvement on wall thickening in the injected ischemic border area of the left ventricle as compared to baseline is shown when the porcine ischemic heart disease model is utilized. Results are shown for pigs injected with plasmid alone (pCK; lane 1), non-lyophilized pCK-HGF-X7 containing 0.9% NaCl (NL-HGF-X7; lane 2), and pCK-HGF-X7 lyophilized with 1.1% sucrose and 0.9% NaCl (L-HGF-X7; lane 3).

In each treatment group, the changes in the segmental wall-thickening before and after the DNA administration were also compared. On Day 26, the average values of the segmental wall-thickening were 24.7±16.5, 33.4±15.9 and 16.5±15.9% for pCK, NL-HGF-X7 and L-HGF-X7 treated group, respectively, and there were no significant inter-group differences (p=NS). On Day 54, the average value of segmental wall-thickening for pCK, NL-HGF-X7 and L-HGF-X7 treatment group was 27.9±18.4, 43.1±11.8, and 30.2±10.7%, respectively. When the magnitude of the percent increase in the segmental wall-thickening from baseline value was compared between the treatment groups, the percent increase in the L-HGF-X7 treatment group was 83.54%, which was significantly higher than that of the NL-HGF-X7 group (28.99%) (FIG. 5).

These results indicate that the intramyocardial administration of the lyophilized formulation (L-HGF-X7) can more efficiently increase the regional blood flow and wall-thickening in the injected ischemic border area of left ventricle compared to the non-lyophilized formulation (NL-HGF-X7). Without wishing to be bound by theory, this is likely due to angiogenic and antifibrotic activities of expressed HGF-X7.

3. Summary

The segmental perfusion and wall-thickening were significantly increased in the lyophilized pCK-HGF-X7 treated group as compared to those of the non-lyophilized pCK and pCK-HGF-X7 treated groups.

These results demonstrate that the intramyocardial administration of pCK-HGF-X7 lyophilized with 1.1% sucrose and 0.9% NaCl to the affected pigs could efficiently and stably increase the regional perfusion and the wall-thickening in the ischemic myocardium as compared to non-lyophilized pCK-HGF-X7.

While the invention has been described with respect to the above specific embodiments, it should be recognized that various modifications and changes may be made to the invention by those skilled in the art which also fall within the scope of the invention as defined by the appended claims.

What is claimed is:

1. A method of administering a DNA composition to a subject comprising administering to said subject a composition reconstituted from a lyophilized DNA formulation comprising, prior to lyophilization,
   (a) a plasmid DNA comprising a hybrid HGF construct wherein the hybrid HGF construct comprises:
      (i) a first cDNA which has the same sequence as exons 1-4 of the human HGF gene wherein said exons 1-4 are arranged in sequential order without an intron therebetween, or degenerates thereof which do not alter the amino acid sequence encoded by said first cDNA,
      (ii) a polynucleotide that has the same sequence as intron 4 of a HGF gene or a fragment thereof, and
      (iii) a second cDNA which has the same sequence as exons 5-18 of the human HGF gene wherein said exons 5-18 are arranged in sequential order without an intron therebetween, or degenerates thereof which do not alter the amino acid sequence encoded by said second cDNA,
      wherein (ii) is located between (i) and (iii) and the hybrid HGF construct simultaneously encodes two heterotypes of human HGF, wherein said plasmid DNA is not complexed to a liposome,
   (b) a salt and
   (c) a carbohydrate,
   wherein said administration is intramuscular and HGF expression from the reconstituted lyophilized DNA formulation is higher than expression from said hybrid HGF construct in non-lyophilized form.

2. The method of claim 1, wherein said DNA composition is administered to said subject for treating or preventing an ischemic disease or a liver disease in said subject.

3. The method of claim 1, wherein said carbohydrate is a mono-, oligo-, or polysaccharide selected from the group consisting of sucrose, glucose, lactose, trehalose, arabinose, pentose, ribose, xylose, galactose, hexose, idose, mannose, talose, heptose, fructose, gluconic acid, sorbitol, mannitol, methyl a-glucopyranoside, maltose, lactone, sorbose, glucaric acid, erythrose, arabinose, allose, altrose, gulose, erythrulose, ribulose, xylulose, psicose, tagatose, glucuronic acid, galacturonic acid, mannuronic acid, glucosamine, galactosamine, neuraminic acid, arabinans, fructans, fucans, galactans, galacturonans, glucans, mannans, xylans, levan, fucoidan, carrageenan, galactocarolose, pectins, pectic acids, amylose, pullulan, glycogen, amylopectin, cellulose, dextran, pustulan, chitin, agarose, keratin, chondroitin, dermatan, hyaluronic acid, alginic acid, xantham gum, starch, and admixtures thereof.

4. The method of claim 3, wherein said carbohydrate is selected from the group consisting of sucrose, mannitol, and admixtures thereof.

5. The method of claim 1, wherein said carbohydrate is in an amount of between about 0.05% to about 30%.

6. The method of claim 1, wherein said salt is selected from the group consisting of NaCl, KCl, and admixtures thereof.

7. The method of claim 1, wherein said salt is in an amount of between about 0.01% and 10%.

8. The method of claim 1, wherein said hybrid HGF construct is selected from the group consisting of HGF-X2, HGF-X3, HGF-X6, HGF-X7, and HGF-X8.

9. The method of claim 8, wherein said hybrid HGF construct is HGF-X7.

10. The method of claim 1, wherein said plasmid DNA is selected from the group consisting of: pCK-HGF-X2, pCK-HGF-X3, pCK-HGF-X6, pCK-HGF-X7, pCK-HGF-X8, pCP-HGF-X2, pCP-HGF-X3, pCP-HGF-X6, pCP-HGF-X7, and pCP-HGF-X8.

11. The method of claim 1, wherein said plasmid DNA of the reconstituted composition is at a concentration of from about 1 ng/mL to about 30 mg/mL.

12. The method of claim 1, wherein said lyophilized DNA formulation is reconstituted in a pharmaceutically acceptable solution.

13. The method of claim 12, wherein said pharmaceutically acceptable solution is selected from the group consisting of water, PBS, TE, Tris buffer, and normal saline.

14. The method of claim 1, wherein said plasmid DNA is a naked DNA.

15. The method of claim 1, wherein said reconstituted composition is administered by direct injection to the muscle.

16. The method of claim 2, wherein the ischemic disease is coronary artery disease (CAD) or peripheral artery disease (PAD).

17. A method of administering a DNA composition to a subject comprising administering to said subject a composition reconstituted from a lyophilized DNA formulation comprising, prior to lyophilization,
   (a) a plasmid DNA comprising a hybrid HGF construct wherein the hybrid HGF construct comprises:
      (i) a first cDNA which has the same sequence as exons 1-4 of the human HGF gene wherein said exons 1-4 are arranged in sequential order without an intron therebetween, or degenerates thereof which do not alter the amino acid sequence encoded by said first cDNA,
      (ii) a polynucleotide that has the same sequence as intron 4 of a HGF gene or a fragment thereof, and
      (iii) a second cDNA which has the same sequence as exons 5-18 of the human HGF gene wherein said exons 5-18 are arranged in sequential order without an intron therebetween, or degenerates thereof which do not alter the amino acid sequence encoded by said second cDNA,
      wherein (ii) is located between (i) and (iii) and the hybrid HGF construct simultaneously encodes two heterotypes of human HGF, wherein said plasmid DNA is non-complexed,
   (b) a salt selected from the group consisting of NaCl and KCl in an amount of between about 0.01% and 10%,
   (c) a carbohydrate selected from the group consisting of sucrose, glucose, lactose, trehalose, arabinose, pentose, ribose, xylose, galactose, hexose, idose, mannose, talose, heptose, fructose, gluconic acid, sorbitol, mannitol, methyl a-glucopyranoside, maltose, lactone, sorbose, glucaric acid, erythrose, arabinose, allose, altrose, gulose, erythrulose, ribulose, xylulose, psicose, tagatose, glucuronic acid, galacturonic acid, mannuronic acid, glucosamine, galactosamine, neuraminic acid, arabinans, fructans, fucans, galactans, galacturonans, glucans, mannans, xylans, levan, fucoidan, carrageenan, galactocarolose, pectins, pectic acids, amylose, pullulan, glycogen, amylopectin, cellulose, dextran, pustulan, chitin, agarose, keratin, chondroitin, dermatan, hyaluronic acid, alginic acid, xantham gum, and starch in an amount of between about 0.05% to about 30%, wherein said administration is intramuscular and HGF expression from the reconstituted lyophilized DNA formulation is higher than expression from said hybrid HGF construct in non-lyophilized form.

18. The method of claim 17, wherein said hybrid HGF construct is selected from the group consisting of HGF-X2, HGF-X3, HGF-X6, HGF-X7, and HGF-X8.

19. The method of claim 17, wherein said DNA composition is administered to said subject for treating or preventing an ischemic disease or a liver disease in said subject.

20. The method of claim 17, wherein said reconstituted composition is administered by direct injection to the muscle.

* * * * *